United States Patent [19]
Davies et al.

[11] Patent Number: 6,037,498
[45] Date of Patent: Mar. 14, 2000

[54] CHIRAL SYNTHESES

[75] Inventors: Stephen Graham Davies, Oxford; Mario Eugenio Cosamino Polywka, Didcot; David Roy Fenwick, South Benfleet; Frank Reed, Wirral, all of United Kingdom

[73] Assignee: Oxford Asymmetry International PLC, Abingdon, United Kingdom

[21] Appl. No.: 08/663,257

[22] PCT Filed: Dec. 28, 1994

[86] PCT No.: PCT/GB94/02827

§ 371 Date: Aug. 12, 1996

§ 102(e) Date: Aug. 12, 1996

[87] PCT Pub. No.: WO95/18134

PCT Pub. Date: Jul. 6, 1995

[30] Foreign Application Priority Data

Dec. 24, 1993 [GB] United Kingdom ............ 9326403

[51] Int. Cl.$^7$ .................. C07C 209/68; C07C 211/26
[52] U.S. Cl. .................. 564/392; 540/200; 544/172; 548/215; 549/494; 560/38; 560/39; 560/41
[58] Field of Search .................. 540/200; 544/172; 548/215; 549/494; 560/38, 39, 41; 564/392

[56] References Cited

U.S. PATENT DOCUMENTS 5,773,610  6/1998  McWhorter et al. ............ 540/200

OTHER PUBLICATIONS

Martin et al., "Total Synthesis of Racemic Lycoramine," J. Org. Chem., 46, 3567–3568, 1981.

Bailey et al., *Tetrahedron Letters,* vol. 30, No. 39, 1989, 5341–5344.

Cardillo et al., *Tetrahedron Letters,* vol. 47, No. 12, 1991, 2263–2272.

*Primary Examiner*—Peter O'Sullivan
*Attorney, Agent, or Firm*—Bacon & Thomas

[57] ABSTRACT

This invention relates to novel compounds of general formula (I)

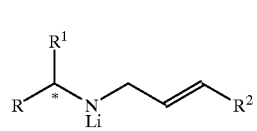

wherein $R^1$ represents an organic group, $R^2$ represents a hydrogen atom or an organic group, and the asterisk denotes that the group $R^1$ is predominantly in the R- or S-configuration such that the compound is in substantially enantiomerically pure form. The compounds are a useful source of chiral nucleophiles, e.g. undergoing stereoselective Michael addition to α,β-unsaturated carboxylic acid derivatives.

12 Claims, No Drawings

CHIRAL SYNTHESES

This invention is concerned with new chiral lithium amides and their use in the synthesis of chiral β-amino acids, β-lactams and the like.

Compounds such as (R)- and (S)-α-methylbenzylamine are known to be useful starting materials in the synthesis of a range of chiral molecules. Thus, for example, N-allyl derivatives thereof have been described in connection with stereoselective syntheses by Bailey et al. in Tet. Lett. 30(39), pp. 5341–5344 (1989) and by Cardillo et al. in Tet. 47(12/13), pp. 2263–2272 (1991).

The present invention is based on our finding that lithio derivatives of such substantially enantiomerically pure N-allylated α-methylbenzylamines and analogues thereof are particularly useful reagents acting as sources of chiral nucleophiles.

Thus according to one aspect of the invention there are provided compounds of general formula (I)

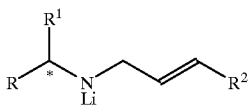

(I)

(wherein R represents a carbocyclic aryl group, $R^1$ represents an organic group, $R^2$ represents a hydrogen atom or an organic group, and the asterisk denotes that the group $R^1$ is predominantly in the R- or S-configuration such that the compound (I) is in substantially enantiomerically pure form).

The term substantially enantiomerically pure as used herein denotes compounds containing at least 80%, advantageously at least 90%, and preferably at least 95% of the desired enantiomer.

Carbocyclic aryl groups R may, for example, contain 6–20 carbon atoms, e.g. as in phenyl or naphthyl, and may if desired be substituted, for example by one or more of halo (e.g. chloro, bromo, or iodo), hydroxy, lower (e.g. $C_{1-4}$) alkoxy (e.g. methoxy or ethoxy), lower alkylthio (e.g. methylthio), lower alkylsulphonyl (e.g. methylsulphonyl), amino, substituted amino (e.g. mono- or di-(lower alkyl) amino such as methylamino or dimethylamino), carboxy, cyano, lower alkoxycarbonyl (e.g. methoxycarbonyl), carbamoyloxy, sulphamoyl and sulphoxy. Preferred R groups include phenyl and 3,4-dimethoxyphenyl.

The groups $R^1$ can be selected from a wide range of organic groupings, including, for example, aliphatic, cycloaliphatic and araliphatic groups, e.g. containing up to 20 carbon atoms and optionally carrying one or more substituents. $R^1$ may thus, for example, represent a group selected from $C_{1-10}$ alkyl such as methyl or ethyl; $C_{2-10}$ alkenyl such as vinyl or propenyl; $C_{3-10}$ cycloalkyl such as cyclopentyl or cyclohexyl; $C_{3-10}$ cycloalkyl—$C_{1-4}$ alkyl such as cyclopentylmethyl; $C_{6-12}$ aryl—$C_{1-4}$ alkyl such as benzyl; and substituted versions of any of the preceding groups, e.g. carrying substituents as described above for R.

One preferred class of compounds (I), by virtue of ease of availability of starting materials therefor, are those in which R represents optionally substituted phenyl and $R^1$ represents methyl.

Where $R^2$ in formula (I) represents an organic group this may, for example, be a lower alkyl group containing 1–10, e.g. 1–6 carbon atoms, as in methyl, ethyl, propyl and butyl groups; a lower (e.g. $C_{2-10}$) alkenyl group such as vinyl; a carbocyclic aryl group, e.g. containing 6–20 carbon atoms, such as phenyl or naphthyl; or a heterocyclic group, e.g. having one or more 5- and/or 6-membered rings and containing one or more heteroatoms selected from O, N and S as in, for example, furyl, thienyl, pyrrolyl, pyridyl, benzothienyl, indolyl, imidazolidinyl or piperidinyl.

As noted above, compounds (I) according to the invention are a useful source of chiral nucleophiles, capable of undertaking highly stereoselective reactions. Thus, for example, they may undergo Michael addition to α,β-unsaturated carboxylic acid derivatives such as esters, thioesters, amides, thioamides and oxazolidinones, with high diastereoselectivity, e.g. as represented by the following sequences in the case of addition to an α,β-unsaturated ester:

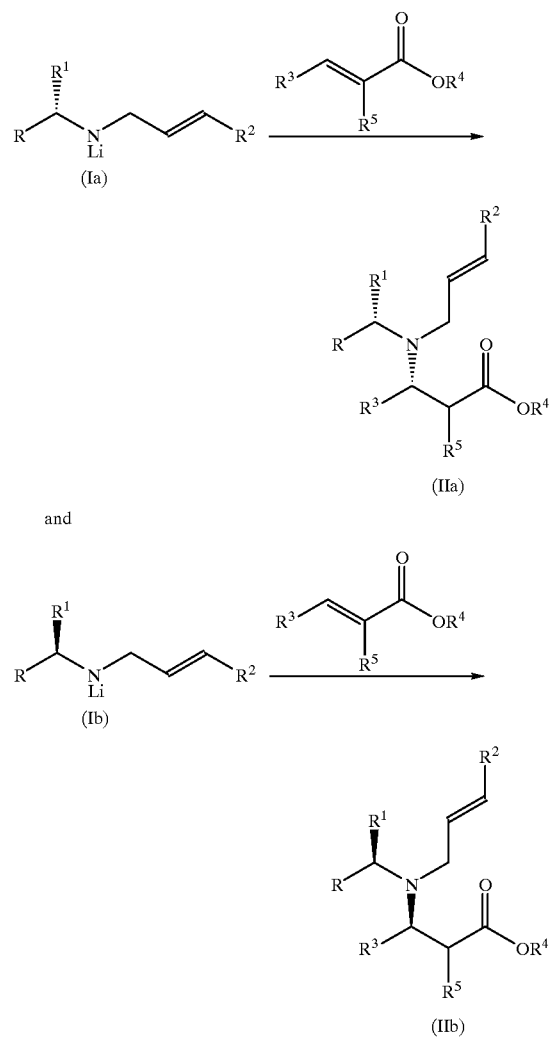

and

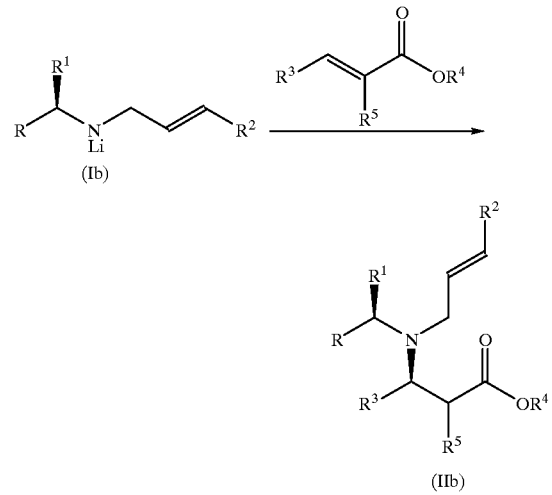

(where R, $R^1$ and $R^2$ are as hereinbefore defined; $R^3$ represents an organic group; $R^4$ represents an esterifying group such as a lower alkyl or aralkyl group; and $R^5$ represents a hydrogen atom or an organic group).

In the above formulae $R^3$ may, for example, be an organic group as hereinbefore described for R, $R^1$ or $R^2$, and may if desired be substituted, e.g. by one or more functional groups such as protected hydroxyl, amino or carboxaldehyde.

The esterifying group $R^4$ in the starting α,β-unsaturated ester is preferably chosen to be relatively bulky, e.g. being a tert-butyl group, in order to minimise competing 1,2-addition of the chiral nucleophile to the carbon atom of the ester carbonyl group.

Where $R^5$ represents an organic group this may, for example, be as described for any of R, $R^1$, $R^2$ and $R^3$.

It will be appreciated that such Michael additions proceed through an enolate intermediate. This may, if desired, be trapped by reaction with an electrophile, for example an alkyl halide, an aldehyde, an imine, a Michael acceptor, or an oxygen electrophile (e.g. molecular oxygen, an epoxide or an oxaziridine—use of such reagents may, for example, permit stereospecific hydroxylation of the carbon atom α- to the ester grouping).

Reaction sequences of the above types and the products thereof, e.g. compounds of formula (IIa) and (IIb) are novel and represent further features of the invention.

The allylic N-substituent $R^2.CH:CH.CH_2$— in compounds of formulae (IIa) and (IIb) may readily and selectively be removed, e.g. under mildly reductive conditions, for example using an agent such as tris(triphenylphosphine)-rhodium(I) chloride in a solvent such as aqueous acetonitrile, and the resulting secondary amine may be subjected to β-lactam formation, e.g. according to the sequence

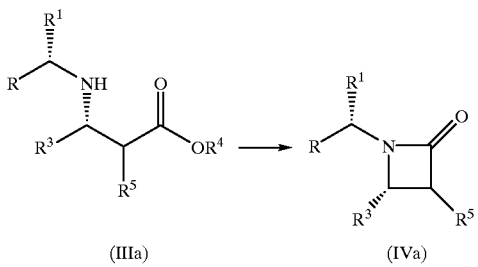

(IIIa) (IVa)

or or

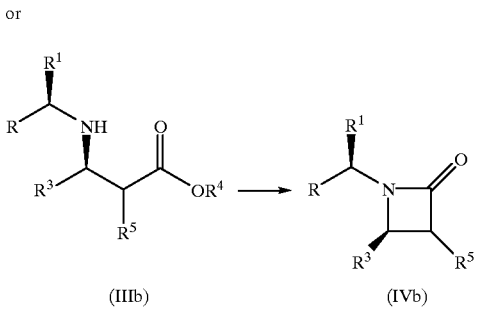

(IIIb) (IVb)

It may be advantageous to subject the secondary amine (IIIa) or (IIIb) to transesterification prior to β-lactam formation, e.g. using techniques standard in the art, such as acid-catalysed transesterification, in order to introduce a less labile esterifying group $R^{4'}$ which will enhance elimination of the —$OR^{4'}$ moiety; representative esterifying groups for this purpose include, for example, methyl and ethyl.

Cyclisation of a compound (IIIa) or (IIIb) to form the desired β-lactam (IVa) or (IVb) may be effected using any convenient cyclisation agent, for example an appropriate organometallic compound, e.g. a Grignard reagent such as methyl magnesium bromide. Such reactions may conveniently be effected in an aprotic organic solvent, for example an ether such as diethyl ether.

N-allyl compounds (IIa) and (IIb) prepared as described above may also be cyclised in accordance with the invention, e.g. using methods generally known in the art, for example to generate 5- and 6-membered heterocycles.

The preparation of β-lactams of formulae (IVa) and (IVb) by the above-described processes is novel and represents a further feature of the present invention.

Compounds of formula (I) in accordance with the invention may conveniently be prepared from a corresponding amine of formula (V)

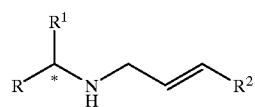

(V)

(where R, $R^1$, $R^2$ and the asterisk are as hereinbefore defined), e.g. by reaction with a lithium alkyl such as n-butyllithium, for example in a cyclic ether solvent such as tetrahydrofuran at a temperature of less than 0° C., conveniently at about −78° C. The thus-formed compound (I) may advantageously be used in situ without being isolated.

Starting materials of formula (V) may themselves be prepared by, for example, converting an amine of formula (VI)

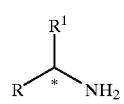

(VI)

(where R, $R^1$ and the asterisk are as hereinbefore defined) to a corresponding lithium amide, e.g. by reaction with a lithium alkyl as described above, and reacting this with an allyl derivative of formula (VII)

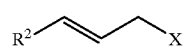

(VII)

(where $R^2$ is as hereinbefore defined and X represents a halogen atom such as bromine) e.g. using as solvent an alcohol such as methanol.

The following non-limitative examples serve to illustrate the invention.

Formulae for Examples

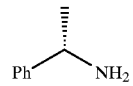

(1)

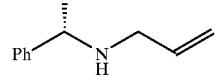

(2)

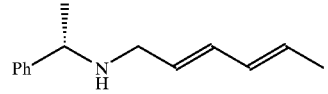

(3)

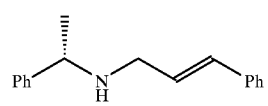

(4)

(5) 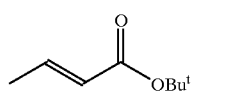
(6) 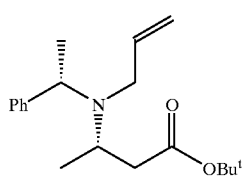
(7) 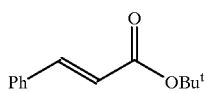
(8) 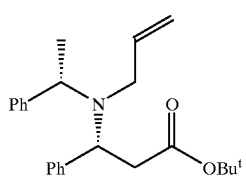
(9) 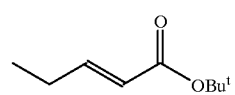
(10) 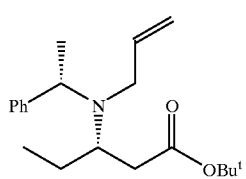
(11) 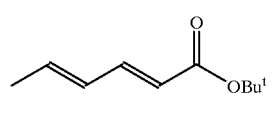
(12) 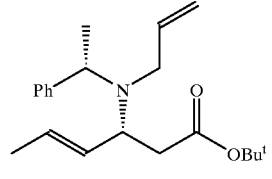
(13) 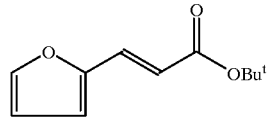
(14) 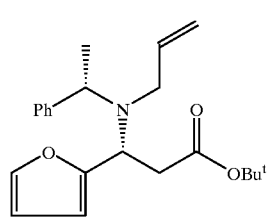
(15) 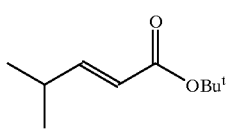
(16)
(17)
(18)
(19)
(20)
(21)
(22)

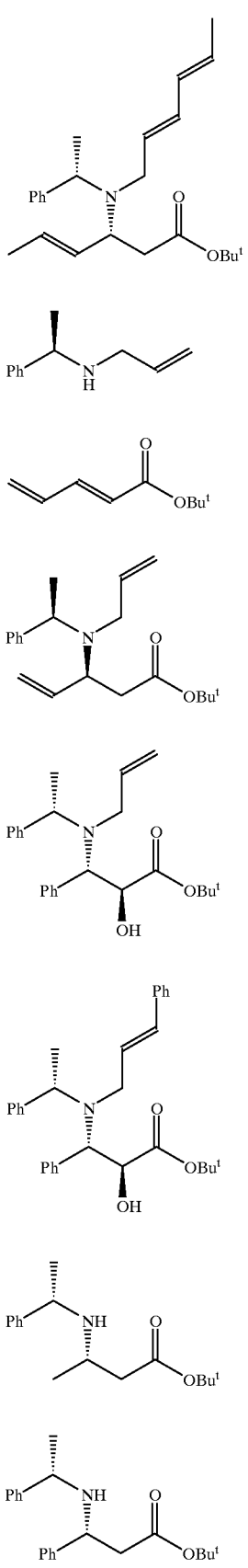

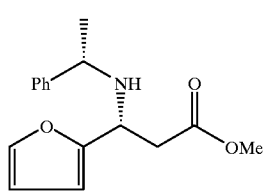
(39)
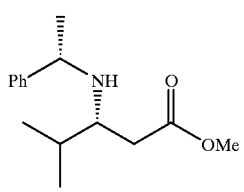
(40)
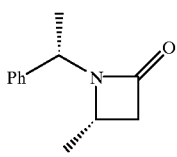
(41)
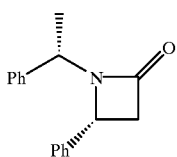
(42)
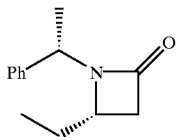
(43)
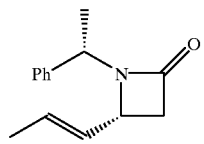
(44)
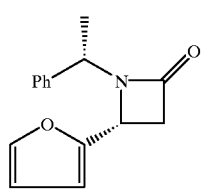
(45)
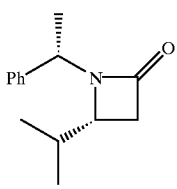
(46)
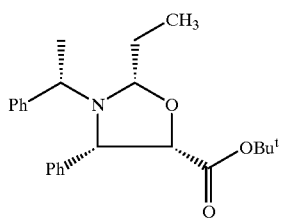
(47)
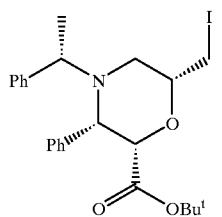
(48)
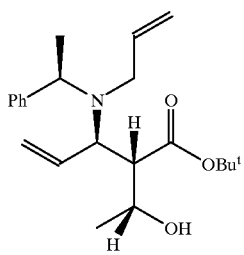
(49)
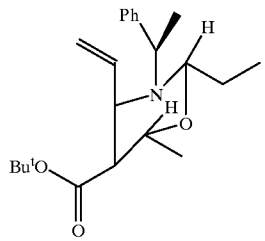
(50)
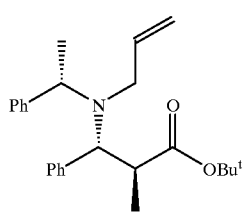
(51)
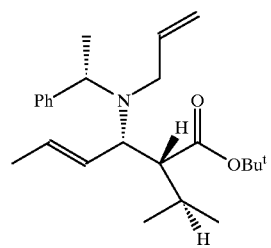
(52)

-continued

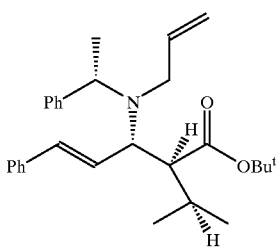
(53)

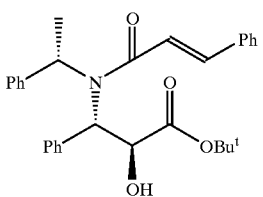
(54)

Preparation of starting materials
Preparation 1
(S)-N-Allyl-α-methylbenzylamine (2)

A solution of (S)-α-methylbenzylamine (1) (10.0 g, 82.5 mmol) in anhydrous tetrahydrofuran (100 ml) was cooled to 0° C. and 1.6 M butyllithium (61 ml, 90.8 mmol) was added dropwise via a syringe. The resulting orange lithium amide solution was stirred for 30 minutes at 0° C., after which allyl bromide (7.2 ml, 99.0 ml) was added. The reaction mixture was stirred for a futher 4 hours at 0° C. and then quenched with methanol. The solvent was removed under reduced pressure to afford an orange residue. This was diluted with ethyl acetate (100 ml) and washed with saturated sodium bicarbonate (2×50 ml), water (50 ml) and brine (50 ml), dried (magnesium sulphate) and filtered, and the solvent was evaporated under reduced pressure. Purification of the residue by silica gel chromatography [ethyl acetate/petroleum ether (1:4); $R_f$ 0.25] afforded the mono-allylated amine as an orange oil. Distillation [110° C., 20 mmHg] gave the title compound (2) as a colourless oil (8.6 g, 65%). $[\alpha]_D^{21}$ −63.2 (c 1.36, CHCl$_3$); $\nu$max(CHCl$_3$)/cm$^{-1}$ 1643 m (C=C); $\delta_H$ (300 MHz; CDCl$_3$) 7.42–7.22 (5H, m, Ph), 5.93 (1H, ddt, J=17.2, 10.2 and 6.0, CH=CH$_2$), 5.16 (1H, dd, J=17.2 and 1.5, trans CH=CH$_2$), 5.10 (1H, d, J=10.2, cis CH=CH$_2$), 3.83 (1H, q, J=6.6, PhCHCH$_3$), 3.13 (2H, d, J=6.1, NCH$_2$), 1.40 (3H, d, J=6.6, PhCHCH$_3$); $\delta_C$ (50 MHz; CDCl$_3$) 145.80 (Ph:C$_{ipso}$), 137.26 (CH=CH$_2$), 128.67, 126.85 (Ph:C$_{ortho}$, C$_{meta}$), 127.14 (Ph:C$_{para}$), 115.84 (CH=CH$_2$), 57.56 PhCHCH$_3$),50.24 (NCH$_2$), 24.23 (PhCHCH$_3$); m/z (CI) 162 (MH$^+$, 100%), 146 (50), 105 (12), 58 (20); (Found: C, 82.07; H, 9.11; N, 8.99. C$_{11}$H$_{15}$N requires C, 81.94; H,9.38; N, 8.69%).

Preparation 2
(S)-(E,E)-N-Hexa-2,4-dienyl-α-methylbenzylamine (3)

To a solution of (S)-α-methylbenzylamine (1) (1.00 g, 8.25 mmol) in ethanol (20 ml) was added 2,4-hexadienal (0.833 g, 8.66 mmol) and the resulting mixture was refluxed for 1 hour. The solution was cooled to 0° C. and sodium borohydride (0.468 g, 12.38 mmol) was slowly added in portions. This solution was allowed slowly to warm to room temperature overnight (16 hours) after which the ethanol was removed under reduced pressure and the residue dissolved in ethyl acetate (50 ml). This solution was washed with brine (30 ml), dried (magnesium sulphate), filtered and evaporated to give an orange oil. This was purified by flash chromatography on silica gel [ethyl acetate/petroleum ether (1:4)], followed by distillation under reduced pressure [130° C. 1 mmHg] to afford the title compound (3) as a colourless oil (1.51 g, 91%), $\delta_H$ (300 MHz; CDCl$_3$) 7.37–7.21 (5H, m, Ph), 6.08 (2H, m, CH=CH—CH=CH), 5.63 (2H, m, CH=CH—CH=CH), 3.80 (1H, q, J=6.6, PhCHCH$_3$), 3.10 (2H, d, J=6.5, NCH$_2$), 1.74 (3H, d, J=6.8, CH=CHCH$_3$), 1.49 (1H, br s, NH), 1.36 (3H, d, J=6.8, PhCHCH$_3$).

Preparation 3
(S)-N-cinnamyl-α-methylbenzylamine (4)

To a solution of (S)-α-methylbenzylamine (1) (0.500 g, 4.13 mmol) in toluene (20 ml) were added N-ethyldiisopropylamine (0.719 ml, 4.13 mmol) and cinnamyl chloride (0.575 ml, 4.13 mmol). The mixture was refluxed overnight, after which the toluene was removed under reduced pressure. The residue was partitioned between ethyl acetate (50 ml) and saturated sodium bicarbonate solution (30 ml) and the organic layer was washed with brine (30 ml), dried (magnesium suphate) and removed under reduced pressure to afford a yellow oil. This was purified by flash chromatography on silica gel [ethyl acetate/ petroleum ether (1:4) to give the title compound (4) as a colourless oil (0.456 g, 47%). $\delta_H$ (200 MHz; CDCl$_3$) 7.41–7.20 (10H, m, Ph), 6.50 (1H, d, J=15.9, PhCH=CH), 6.30 (1H, dt, J=15.9 and 6.1, PhCH=CH), 3.88 (1H, q, J=6.6, PhCHCH$_3$), 3.29 (2H, d, J=6.5, NCH$_2$), 1.56 (1H, br s, NH), 1.42 (3H, d, J=6.8, PhCHCH$_3$).

Formation and reaction of chiral lithium amides

EXAMPLE 1

(3S,αS)-t-Butyl 3-(N-allyl-α-methylbenzylamino) butanoate (6)

A solution of (S)-N-allyl-α-methylbenzylamine (2) (0.75 mmol) in anhydrous tetrahydrofuran (5 ml) was cooled to −78° C. and 1.6 M butyllithium (0.60 mmol) was added dropwise via a syringe. The resulting pink lithium amide solution was stirred for 1 hour at −78° C. The Michael acceptor t-butyl crotonate (5) (0.50 mmol) was then slowly added, dropwise, as a solution in anhydrous tetrahydrofuran (2 ml) via a cannula and stirring was continued at −78° C. for a further 1 hour. The reaction was quenched by the addition of saturated aqueous ammonium chloride. The solvent was evaporated under reduced pressure and the residue was diluted with ethyl acetate (30 ml) and washed with water (30 ml) and brine (30 ml), dried (magnesium suphate) and filtered, and the solvent was evaporated under reduced pressure to afford a clear oil. This material was then subjected to flash chromatography on silica gel, to yield the title compound (6). $[\alpha]_D^{21}$ +16.9(c 1.80, CHCl$_3$); $\nu_{max}$ (CHCl$_3$)cm$^{-1}$ 1729 s (C=O), 16.41 m (C=C); $\delta_H$ (300 MHz; CDCl$_3$) 7.39–7.18 (5H, m, Ph), 5.84 (1H, m, CH=CH$_2$), 5.14 (1H, ddd, J=17.2, 3.5 and 1.7, trans CH=CH$_2$), 5.01 (1H, ddd, J=10.1, 3.3 and 1.6, cis CH=CH$_2$), 3.95 (1H, q, J=6.8, PhCHCH$_3$), 3.47 (2H, m, NCH$_2$), 3.16 (1H, m NCHCH$_2$), 2.32, 2.09 (2H, ABX system, $J_{AB}$=14.3, $J_{AX}$=6.1, $J_{BX}$=8.3 CH$_2$CO), 1.42 (9H, s, (CH$_3$)$_3$C), 1.39 (3H, d, J=6.8, PhCHCH$_3$), 1.05 (3H, d, J=6.7, CH$_3$CHCH$_2$); $\delta_C$ (50 MHz; CDCl$_3$) 172.20 (C=O), 145.45 (Ph:C$_{ipso}$), 139.55 (CH=CH$_2$), 128.23, 127.76 (Ph:C$_{ortho}$,C$_{meta}$), (Ph:C), 126.75 (Ph:C$_{para}$), 115.35 (CH=CH$_2$), 79.86 (C(CH$_3$)$_3$), 58.06, 50.67 (CHN), 48.86 (NCH$_2$), 41.20 (CH$_2$CO), 27.98 (C(CH$_3$)$_3$), 19.58, 17.16 (NCHCH$_3$); m/z (CI) 304 (MH$^+$, 100%), 248 (12), 188 (30), 142 (25), 105 (22), 84 (32); (Found: C, 75.03; H, 9.89; N, 4.87. C$_{19}$H$_{29}$NO$_2$ requires C, 75.21; H,9.63; N, 4.62%).

EXAMPLE 2

(3R,αS)-t-Butyl 3-(N-allyl-α-methylbenzylamino)-3-phenylpropionate (8)

The title compound (8) was obtained by repeating the process of Example 1 using t-butyl cinnamate (7) as the Michael acceptor. $[\alpha]_D^{21}$ −2.1 (c 3.24, CHCl$_3$); $\nu_{max}$ (CHCl$_3$)/cm$^{-1}$ 1730 s (C=O), 1641 m (C=C); $\delta_H$ (300 MHz; CDCl$_3$) 7.43–7.19 (10H, m, Ph), 5.81 (1H, m, CH=CH$_2$), 5.15 (1H, ddd, J=17.2, 3.5 and 1.6, trans CH=CH$_2$), 5.04 (1H, ddd, J=10.2, 3.1 and 1.4, cis CH=CH$_2$), 4.45(1H, dd, PhCHCH$_2$), 4.04 (1H, q, J=6.7, PhCHCH$_3$), 3.16 (2H, m,NCH$_2$), 2.78, 2.60 (2H, ABX system, $J_{AB}$=14.7, $J_{AX}$=6.2, $J_{BX}$=8.9 CH$_2$CO), 1.30 (9H, s, (CH$_3$)$_3$C), 1.17 (3H, d, J=6.8, PhCHCH$_3$), $\delta_C$ (50 MHz; CDCl$_3$) 171.59 (C=0), 145.20, 141.92 (Ph:C$_{ipso}$), 139.23 (CH=CH$_2$), 128.39, 128.29, 128.06, 127.80 (Ph:C$_{ortho}$, C$_{meta}$), 127.31, 126.81 (Ph:C$_{para}$), 115.90 (CH=CH$_2$), 80.23 (C(CH$_3$)$_3$), 59.19, 56.21 (CHN), 49.76 (NCH$_2$), 39.17 (CH$_2$CO), 27.84 (C(CH$_3$)$_3$, )16.35 (NCHCH$_3$), m/z (CI) 366(MH$^+$, 100%), 310 (8), 250 (15), 160 (35), 146 (30), 105 (25); Found: C, 78.77; H, 8.81; N, 3.62. C$_{24}$H$_{31}$NO$_2$ requires C, 78.87; H,8.55; N, 3.83%).

EXAMPLE 3

(3R,αS)-t-Butyl 3-(N-allyl-α-methylbenzylamino) pentanoate (10)

The title compound (10) was obtained by repeating the process of Example 1 using t-butyl 2-pentenoate (9) as the Michael acceptor. $[\alpha]_D^{21}$ +18.5 (c 1.88, CHCl$_3$); $\nu_{max}$ (CHCl$_3$)/cm$^{-1}$ 1729 s (C=O), 1641 m (C=C); $\delta_H$ (300 MHz; CDCl$_3$) 7.36–7.18 (5H, m, Ph), 5.86 (1H, m, CH=CH$_2$), 5.19 (1H, ddd, J=17.2, 3.5 and 1.8, trans CH=CH$_2$), 5.12 (1H, ddd, J=10.2, 3.2 and 1.7, cis CH=CH$_2$), 3.94(1H, q, J=6.9, PhCHCH$_3$), 3.20 (1H, m,CH$_3$CH$_2$CH), 3.15 (2H, m,NCH$_2$), 2.03, 1.96 (2H, ABX system, $J_{AB}$=14.5, $J_{AX}$=5.2, $J_{BX}$=8.3, CH$_2$=CO), 1.41 (9H, s, (CH$_3$)$_3$), 1.40 (3H, d, J=6.9, PhCHCH$_3$), 1.40 (2H, m, CH$_3$CH$_2$), 0.92 (3H, t, J=7.3, CH$_3$CH$_2$); $\delta_C$ (50 MHz; CDCl$_3$) 172.65 (C=O), 144.61 (Ph:C$_{ipso}$), 139.60 (CH=CH$_2$), 128.24, 127.91 (Ph:C$_{ortho}$, C$_{meta}$), 126.88 (Ph:C$_{para}$), 115.35 (CH=CH$_2$), 79.82 (C(CH$_3$)$_3$), 58.28, 56.32 (CHN), 48.74 (NCH$_2$), 37.87 (CH$_2$CO), 27.96 (C(CH$_3$)$_3$), 25.67 (CH$_3$CH$_2$), 20.66 (NCHCH$_3$), 11.60 (CH$_3$CH$_2$); m/z (CI) 318 (MH$^+$, 100%), 288 (8), 262 (10), 202 (12), 105 (15); (Found: C, 75.88; H, 9.71; N, 4.42. C$_{20}$H$_{31}$NO$_2$ requires C, 75.67; H, 9.84; N, 4.41%).

EXAMPLE 4

(3R,αS)-t-Butyl 3-(N-allyl-α-methylbenzylamino)-4-hexenoate (12)

The title compound (12) was obtained by repeating the process of Example 1 using t-butyl sorbate (11) as the Michael acceptor. $[\alpha]_D^{21}$ +2.7 (c 1.67, CHCl$_3$); $\nu_{max}$ (CHCl$_3$)/CM$^{-1}$ 1729 s (C=O), 1656 m (C=C), 1644 m (C=C); $\delta_H$ (300 MHz, CDCl$_3$) 7.39–7.18 (5H, m, Ph), 5.79 (1H, m, CH=CH$_2$), 5.51 (2H, m, CH$_3$CH=CH), 5.08 (1H, ddd, J=17.2, 3.4 and 1.7, trans CH=CH$_2$), 5.00 (1H, ddd, J=10.1, 3.1 and 1.5, cis CH=CH$_2$), 4.01 (1H, q, J=6.8, PhCHCH$_3$), 3.83 (1H, m, CHCH$_2$CO), 3.13 (2H, m, NCH$_2$), 2.42, 2.27 (2H, ABX system, $J_{AB}$=14.2, $J_{AX}$=6.5, $J_{BX}$=8.4, CH$_2$CO), 1.71 (3H, d, J=5.0, CH$_3$C=C), 1.41 (9H, s, (CH$_3$)$_3$C), 1.38 (3H, d, J=6.8, PhCHCH$_3$); $\delta_C$ (50 MHz; CDCl$_3$) 171.66 (C=O), 145.50 (Ph:C$_{ipso}$), 139.19 (CH=CH$_2$), 130.93 (CH$_3$C=C), 128.16, 127.80 (Ph:C$_{ortho}$, C$_{meta}$), 126.99, 126.67 (Ph:C$_{para}$, CH$_3$C=C), 115.54 (CH=CH$_2$), 79.94 (C(CH$_3$)$_3$), 57.22, 57.07 (CHN), 49.62 (NCH$_2$), 39.83 (CH$_2$CO), 27.97 (C(CH$_3$)$_3$), 18.36, 17.84 (CH$_3$C=C, NCHCH$_3$); m/z (CI) 330 (MH$^+$, 100%), 274 (10), 214 (35), 110 (25).

EXAMPLE 5

(3R,αS)-t-Butyl 3-(N-allyl-α-methylbenzylamino)-3-(fur-2-yl)-propionate (14)

The title compound (14) was obtained by repeating the process of Example 1 using t-butyl 3-(fur-2-yl)propenoate (13) as the Michael acceptor. $\nu_{max}$ (CHCl$_3$)/cm$^{-1}$ 1729 s (C=O), 1641 m (C=C); $\delta_H$ (300 MHz; CDCl$_3$) 7.41–7.18 (6H, m, Ph, OCH=CH), 6.35 (1H, dd, J=1.9 and 3.2, OCH=CH), 6.14 (1H, d, J=3.2, OC=CH), 5.69 (1H, m,CH=CH$_2$), 5.10 (1H, dd, J=17.2 and 1.6, trans CH=CH$_2$), 5.04 (1H, dd, J=10.2 and 1.6, cis CH=CH$_2$), 4.60 (1H, t, J=7.6, NCHCH$_2$), 4.08 (1H, q, J=6.8, PhCHCH$_3$), 3.14 (2H, m,NCH$_2$), 2.78, 2.69 (2H, ABX system, $J_{AB}$=15.0, $J_{AX}$=8.0, $J_{BX}$=7.4, CH$_2$=CO), 1.42 (9H, s, (CH$_3$)$_3$), 1.10 (3H, d, J=6.8,PhCHCH$_3$); $\delta_C$ (50 MHz; CDCl$_3$) 170.98 (C=O), 155.32 (OC=CH), 145.64 (Ph:C$_{ipso}$), 141.59 (OCH), 138.30 (CH=CH$_2$), 128.20, 127.76 (Ph:C$_{ortho}$,C$_{meta}$), 126.68 (Ph:C$_{para}$), 116.42, (CH=CH$_2$), 110.32 (OCH=CH), 107.16 (OCH=CH), 80.38 (C(CH$_3$)$_3$), 56.29, 51.86 (CHN), 50.09 (NCH$_2$), 38.41 (CH$_2$CO), 27.96 (C(CH$_3$)$_3$), 16.91 (NCHCH$_3$); m/z (CI) 356 (MH$^+$, 100%), 300 (10), 240 (20), 194 (10), 160 (25).

EXAMPLE 6

(3R,αS)-t-Butyl 3-(N-allyl-α-methylbenzylamino)-4-methylpentanoate (16)

The title compound (16) was obtained by repeating the process of Example 1 using t-butyl 4-methyl-2-pentenoate (15) as the Michael acceptor. $[\alpha]_D^{21}$ +52.7 (c 1.85, CHCl$_3$); $\nu_{max}$ (CHCl$_3$)/cm$^{-1}$ 1729 s (C=O), 1641w (C=C); $\delta_H$ (300 MHz; CDCl$_3$) 7.34–7.20 (5H, m, Ph), 5.87 (1H, m, CH=CH$_2$), 5.23 (1H, ddd, J=17.2, 3.2 and 1.8, trans CH=CH$_2$), 4.88 (1H, dd, J=10.1 and 1.0, cis CH=CH$_2$), 3.91 (1H, q, J=7.0, PhCHCH$_3$), 3.15 (1H, m, CHCH$_2$CO), 3.10 (2H,m,NCH$_2$), 1.97, 1.87 (2H, ABX system, $J_{AB}$=16.0, $J_{AX}$=8.3, $J_{BX}$=3.2, CH$_2$CO), 1.63 (1H, m, (CH$_3$)$_2$CH), 1.42 (3H, d, J=7.0, PhCHCH$_3$), 1.41 (9H, s, (CH$_3$)$_3$C), 1.00 (3H, d, J=6.6, (CH$_3$)$_2$CH), 0.83 (3H, d,(CH$_3$)$_2$CH); $\delta_c$ (50 MHz; CDCl$_3$) 172.86 (C=0), 143.52, (Ph:C$_{ipso}$), 139.43 (CH=CH$_2$), 128.20, 128.12 (Ph:C$_{ortho}$,C$_{meta}$), 126.92, (Ph:C$_{para}$), 115.46 (CH=CH$_2$), 79.82 (CCH$_3$)$_3$), 58.97, 58.42 (CHN), 49.59 (NCH$_2$), 36.34 (CH$_2$CO), 32.85 (CH$_3$)$_2$CH), 27.89 (C(CH$_3$)$_3$), 20.83, 20.51 ((CH$_3$)$_2$ CH), 19.59 (NCHCH$_3$); m/z (CI) 322 (MH$^+$, 100%), 288 (30), 232 (15), 128 (22), 105 (25); (Found: C, 76.12; H, 10.36. C$_{21}$H$_{33}$NO$_2$ requires C, 76.09; H, 10.03%).

EXAMPLE 7

(3S,αS)-t-Butyl 3-(N-allyl-α-methylbenzylamino)-4-phenylbutanoate (18)

The procedure of Example 1 was repeated using (S)-N-allyl-α-methylbenzylamine (2) (0.750 g, 4.7 mmol), 1.6M butyllithium (2.52 ml, 4.0 mmol) and t-butyl 4-phenyl-2-butenoate (17) (0.678 g, 3.1 mmol) as the Michael acceptor. Flash chromatography on silica gel [ethyl acetate/petroleum ether (1:49)] afforded the title compound (R$_f$ 0.20) as a colourless oil (0.968 g, 82%). $\delta_H$ (300 MHz; CDCl$_3$) 7.40–7.15 (5H, m, Ph), 5.96–5.82 (1H, m, NCH$_2$CH=CH$_2$), 5.19 (1H, dd, J=17.3 and 1.3, trans CH=CH$_2$), 5.09 (1H, dd, J=10.1 and 1.3, cis CH=CH$_2$), 3.95 (1H, q, J=6.7, PhCHCH$_3$), 3.67–3.56 (1H, m, PhCH$_2$CH), 3.38–3.13 (2H, m, NCH$_2$), 2.77 (1H, dd, J=14.7 and 7.1, CH$_2$CO$_2$), 2.55 (1H, dd, J=14.7 and 6.0, CH$_2$CO$_2$), 2.08 (2H, d, J=7.1, PhCH$_2$), 1.42 (9H, s, (CH$_3$)$_3$C), 1.20 (3H, d, J=6.7, PhCHCH$_3$).

EXAMPLE 8

(3R,αS)-t-Butyl 3-(N-allyl-α-methylbenzylamino)-5-phenyl-4-pentenoate (20)

The procedure of Example 1 was repeated using (S)-N-allyl-α-methylbenzylamine (2) (0.840 g, 5.22 mmol), 1.6M butyllithium (2.16 ml, 4.17 mmol) and t-butyl 5-phenyl-(E,E)-pentadienoate (19) (0.800 g, 3.48 mmol) as the Michael acceptor. Flash chromatography on silica gel [ethyl acetate/petroleum ether (1:19)] afforded the title compound (20) as a colourless oil (1.33 g, 98%). $\delta_H$ (200 MHz; CDCl$_3$) 7.48–7.21 (10H, m, Ph), 6.48 (1H, d, J=16.0, PhCH=CH), 6.25 (1H, dd, J=16.0 and 7.4, PhCH=CH), 5.85 (1H, m, NCH$_2$CH=CH$_2$), 5.15 (1H, app. dd, J=17.3 and 1.6, trans NCH$_2$CH=CH), 5.07 (1H, app. dd, J=10.3 and 1.5, cis NCH$_2$CH=CH$_2$), 4.09 (2H, m, PhCHCH$_3$ and PhCH=CHCH), 3.22 (2H, d, J=6.1, NCH$_2$), 2.56 (1H, dd, J=14.3 and 6.6, CH$_2$CO$_2$), 2.42 (1H, dd, J=14.3 and 8.2, CH$_2$CO$_2$), 1.43 (3H, m, PhCHCH$_3$), 1.42 (9H, s, (CH$_3$)$_3$C).

The same diastereoisomer (20) was obtained when t-butyl 5-phenyl(Z,E)-pentadienoate (21) was used as the Michael acceptor.

EXAMPLE 9

(3R,αS)-t-Butyl 3-(N-cinnamyl-α-methylbenzylamino)-3-phenylpropionate (22)

(S)-N-cinnamyl-α-methylbenzylamine (4) (0.100 g, 0.42 mmol), 1.6M butyllithium (0.242 ml, 0.39 mmol) and t-butyl cinnamate (7) (0.072 g, 0.35 mmol) were reacted according to the procedure of Example 1. Flash chromatography of the product on silica gel [ethyl acetate/petroleum ether (1:49)] afforded the title compound ($R_f$ 0.3) as a colourless oil (0.145 g, 78%). $\delta_H$ (300 MHz; CDCl$_3$) 7.50–7.18 (15H, m, Ph), 6.42 (1H, d, J=16.0, PhCH=CH), 6.11 (1H, dt, J=16.0 and 6.2; CH=CHPh), 4.53 (1H, dd, J=8.7 and 6.4, PhCHCH$_2$), 4.07 (1H, q, J=6.7, PhCHCH$_3$), 3.32 (2H, dd, J=6.2 and 1.1, NCH$_2$), 2.83 (1H, dd, J=14.6 and 6.4, CH$_2$CO$_2$), 2.62 (1H, dd, J=14.6 and 8.7, CH$_2$CO$_2$), 1.31 (9H, s, (CH$_3$)$_3$C), 1.27 (3H, d, J=6.7, PhCHCH$_3$).

EXAMPLE 10

(3R,αS)-t-Butyl 3-(N-hexa-2,4-dienyl-α-methylbenzylamino)-4-hexenoate (23)

(S)-(E,E)-N-Hexa-2,4-dienyl-α-methylbenzylamine (3) (0.500 g, 2.49 mmol), 1.6M butyllithium (1.35 ml, 2.16 mmol) and t-butyl sorbate (11) (0.279 g, 1.66 mmol) were reacted according the procedure of Example 1. Flash chromatography of the product on silica gel [ethyl acetate/petroleum ether (1:19)] afforded the title compound as a colourless oil (0.791 g, 72%). $\delta_H$ (200 MHz; CDCl$_3$) 7.39–7.18 (5H, m, Ph), 6.12–5.93 (2H, m, CH=CH—CH=CH), 5.69–5.41 (4H, m, CH$_3$CH=CH and CH=CH—CH=CH), 4.0 (1H, q, J=6.8, PhCHCH$_3$), 3.87–3.75 (1H, m, CH$_3$CH=CHCH), 3.21–3.09 (2H, m, NCH$_2$), 2.40 (1H, dd, J=14.1 and 6.4, CH$_2$CO$_2$), 2.25 (1H, dd, J=14.1 and 8.5, CH$_2$CO$_2$), 1.76– 1.71 (6H, m, CH$_3$CH=CHCH and CH=CHCH$_3$), 1.41 (9H, s, (CH$_3$)$_3$C), 1.37 (3H, d, J=6.7, PhCHCH$_3$).

EXAMPLE 11

(3S,αR)-t-Butyl 3-(N-allyl-α-methylbenzylamino)-4-pentenoate (26)

A solution of (R)-N-allyl-α-methylbenzylamine (24) (1.78 g, 11.1 mmol) in anhydrous tetrahydrofuran (20 ml) was cooled to −78° C. and 1.6M butyllithium (6.00 ml, 9.5 mmol) was added dropwise via a syringe. The resulting orange lithium amide solution was stirred at −78° C. for 1 hour. A solution of t-butyl pentadienoate (25) (1.137 g, 7.4 mmol) in anhydrous tetrahydrofuran (15 ml) was then added via a cannula and the solution was stirred for a further 1 hour. The reaction was quenched by the addition of saturated aqueous ammonium chloride solution and the solution was allowed to warm to room temperature. Ethyl acetate (50 ml) was added, followed by brine (10 ml). The organic layer was separated, dried (magnesium sulphate) and filtered and the solvent evaporated under reduced pressure to afford a pale yellow oil. This was purified by flash chromatography on silica gel [ethyl acetate/petroleum ether (1:49)] to afford the title compound ($R_f$ 0.25) as a colourless oil (1.97 g, 85%). $\delta_H$ (300 MHz; CDCl$_3$) 7.40–7.19 (5H, m, Ph), 5.94–5.74 (2H, m, CH$_2$=CHCH and NCH$_2$CH=CH$_2$), 5.16–5.00 (4H, m, CH$_2$=CHCH and NCH$_2$CH=CH$_2$), 4.02 (1H, q, J=6.8, PhCHCH$_3$), 3.90 (1H, app. q, J=7.1, NCHCH$_2$), 3.15 (2H, d, J=6.1, NCH$_2$CH=CH$_2$), 2.41 (1H, dd, J=6.4 and 14.5, CH$_2$CO$_2$), 2.31 (1H, dd, J=14.5 and 8.3, CH$_2$CO$_2$), 1.42 (9H, s, (CH$_3$)$_3$C), 1.39 (3H, d, J=6.8, PhCHCH$_3$).

EXAMPLE 12

(2S,3S,αS)-t-Butyl 3-(N-allyl-α-methylbenzylamino)-2-hydroxy-3-phenylpropionate (27)

A solution of (S)-N-allyl-α-methylbenzylamine (2) (1.94 g, 12.1 mmol) in anhydrous tetrahydrofuran (25 ml) was cooled to −78° C. and 1.6M butyllithium (6.03 ml, 9.6 mmol) was added dropwise via a syringe. The resulting orange lithium amide solution was stirred at −78° C. for 1 hour. A solution of t-butyl cinnamate (7) (1.64 g, 8.1 mmol) in anhydrous tetrahydrofuran (15 ml) was then added via a cannula and the solution was stirred for a further 1 hour. The resulting yellow enolate solution was then diluted with anhydrous tetrahydrofuran (30 ml) and solid (+)-(camphorsulphonyl)-oxaziridine (2.76 g, 12.1 mmol) was added. After stirring for a further 6 hours at −78° C., the mixture was warmed to 0° C. (15 minutes) and quenched by the addition of saturated aqueous ammonium chloride solution. Ethyl acetate (50 ml) was added, followed by brine (10 ml). The organic layer was separated, dried (magnesium sulphate) and filtered and the solvent was evaporated under reduced pressure to afford an oily solid residue. Treatment of this with diethyl ether precipitated the oxaziridine/sulfonimine which was removed by filtration and the resulting oil was purified by flash chromatography on silica gel [ethyl acetate/petroleum ether (1:19)] affording the title compound ($R_f$ 0.20) as a colourless oil (2.89 g, 95%). $\delta_H$ (300 MHz: CDCl$_3$) 7.50–7.21 (10H, m, Ph), 5.89 (1H, m, NCH$_2$CH=CH$_2$), 5.12 (1H, app. dd, J=17.2 and 41.4, trans CH=CH$_2$), 5.04 (1H, app. dd, J=17.2 and 1.4, cis CH=CH$_2$), 4.53 (1H, d, J=3.8, CHOH), 4.23 (1H, d, J=3.8, NCHCH), 4.13 (1H, q, J=6.8, PhCHCH$_3$), 3.47 (1H, app. dd, J=15.6 and 7.1, NCH$_2$), 3.03 (1H, bs, OH), 1.29 (9H, s, (CH$_3$)$_3$CH), 1.21 (3H, d, J=6.8, PhCHCH$_3$).

EXAMPLE 13

(2S,3S,αS)-t-Butyl 3-(N-cinnamyl-α-methylbenzylamino)-2-hydroxy-3-phenylpropionate (28)

The procedure of Example 12 was repeated using (S)-N-cinnamyl-α-methylbenzylamine (4) (0.300 g, 1.27 mmol), 1.6M butyllithium (0.730 ml, 1.17 mmol), t-butyl cinnamate (7) (0.199 g, 0.97 mmol) and (+)-(camphorsulphonyl)-oxaziridine (0.290 g, 1.27 mmol). Flash chromatography of the product on silica gel [ethyl acetate/petroleum ether (1:19)] afforded the title compound as a colourless oil (0.361 g, 81%). $\delta_H$ (300 MHz; CDCl$_3$) 7.55–7.12 (15H, m, Ph), 6.42 (1H, d, J=16.0, PhCH=CH), 6.25 (1H, dt, J=16.0 and 6.6, CH—CHPh), 4.61 (1H, d, J=4.0, CHCHCO$_2$), 4.32 (1H, d, J=4.0, PhCHCH), 4.20 (1H, q, J=6.8, PhCHCH$_3$), 3.65 (1H, dd, J=15.8 and 5.7, NCH$_2$), 3.47 (1H, dd, J=15.8 and 6.9, NCH$_2$), 3.22 (1H, br s, OH), 1.32 (9H, s, (CH$_3$)$_3$C), 1.29 (3H, d, J=6.8, PhCHCH$_3$).

De-allylation reactions

Standard procedure for de-allylation

A solution of the N-allylated β-amino ester (1.00 mmol) and tris(triphenylphosphine)rhodium(I) chloride (0.05 mmol) in acetonitrile/water (80:20, 50 ml) was prepared in a magnetically stirred 100 cm$^3$ round bottomed flask. A Claisen adaptor fitted with an addition funnel on one arm and a short path distillation head and reflux condenser on the other was then attached to the reaction vessel. The addition funnel was charged with excess acetonitrile/water (80:20) and the system was continually flushed with nitrogen as the reaction was brought to vigorous boiling, fresh solvent being added to replace the volume of liquid swept out of the distillation head. The reaction was refluxed for 2 hours and the solvent was then removed under reduced pressure. The dark brown oily residue was passed through alumina, eluting with diethyl ether, which after removal of solvent under reduced pressure afforded a pale yellow oil. This material was then subjected to flash chromatography on silica gel.

EXAMPLE 14

(3S,αS)-t-Butyl 3-(α-methylbenzylamino)butanoate (29)

The title compound (29) was prepared from compound (6) of Example 1 using the above-described procedure. $[\alpha]_D^{21}$ −36.3 (c 1.78, CHCl$_3$); $\nu_{max}$(CHCl$_3$)/cm$^{-1}$ 1724 s (C=O); $\delta_H$ (300 MHz; CDCl$_3$) 7.36–7.14 (5H, m, Ph), 3.89 (1H, q, J=6.5, PhCHCH$_3$), 2.94 (1H, m, CH$_3$CHCH$_2$), 2.34, 2.28 (2H, ABX system, J$_{AB}$=14.4, J$_{AX}$=5.6, J$_{BX}$=6.2, CH$_2$CO), 1.45 (9H, s, (CH$_3$)$_3$C), 1.33 (3H, d, J=6.6, PhCHCH$_3$), 1.04 (3H, d, J=6.5, CH$_3$CHCH$_2$); $\delta_C$ (50 MHz; CDCl$_3$) 171.98 (C=O), 146.32 (Ph: C$_{ipso}$); 128.60, 126.75 (Ph:C$_{ortho}$, C$_{meta}$), 127.03 (Ph:C$_{para}$), 80.29 (C(CH$_3$)$_3$), 55.13, 47.98 (CHN), 41.86 (CH$_2$CO), 28.03 (C(CH$_3$)$_3$), 24.46, 21.35 (NCHCH$_3$); m/z (CI) 264 (MH$^+$, 100%), 208 (25), 148 (35), 105 (10); (Found: C, 72.93; H, 9.77; N, 5.10. C$_{16}$H$_{25}$NO$_2$ requires C, 72.97; H, 9.57; N, 5.32%).

EXAMPLE 15

(3S,αS)-t-Butyl 3-(α-methylbenzylamino)-3-phenylpropionate (30)

The title compound (30) was prepared from compound (8) of Example 2 using the above-described procedure. $[\alpha]_D^{21}$ −16.3 (c 1.45, CHCl$_3$); $\nu_{max}$ (CHCl$_3$)/cm$^{-1}$ 1728 s (C=O); $\delta_H$ (300 MHz; CDCl$_3$) 7.36–7.18 (10H, m, Ph), 4.17 (1H, dd, J=7.9 and 6.2, NCHCH$_2$), 3.67 (1H, q, J=6.5, PhCHCH$_3$), 2.65, 2.57 (2H, ABX system, J$_{AB}$=14.7, J$_{AX}$= 7.9, J$_{BX}$= 6.5, PhCHCH$_2$); $\delta_C$ (50 MHz; CDCl$_3$) 171.36 (C=O), 146.38, 143.17 (Ph:C$_{ipso}$), 128.66, 127.33, 126.82 (Ph:C$_{ortho}$, C$_{meta}$), 127.46, 127.10 (Ph:C$_{para}$), 80.51 (C(CH$_3$)$_3$), 57.15, 54.57 (CHN), 43.94 (CH$_2$CO), 27.97 (C(CH$_3$)$_3$), 22.29 (NCHCH$_3$); m/z (CI) 326 (MH$^+$, 100%), 270 (20), 210 (30), 120 (25), 106 (28); (Found: C, 77.44; H, 8.59; N, 4.49. C$_{21}$H$_{27}$NO$_2$ requires C, 77.50, H, 8.36; N, 4.30%).

EXAMPLE 16

(3S,αS)-t-Butyl 3-(α-methylbenzylamino)pentanoate (31)

The title compound (31) was prepared from compound (10) of Example 3 using the above-described procedure. $[\alpha]_D^{21}$ −54.0 (c 1.81, CHCl$_3$); $\nu_{max}$(CHCl$_3$)/cm$^{-1}$ 1724 s (C=O); $\delta_H$ (300 MHz; CDCl$_3$) 7.36–7.20 (5H, m, Ph), 3.91 (1H, q, J=6.5, PhCHCH$_3$), 2.68 (1H, m, NCHCH$_2$), 2.39, 2.28 (2H, ABX system, J$_{AB}$=14.3, J$_{AX}$=5.7, J$_{BX}$=5.5, CH$_2$CO), 1.47 (9H, s, (CH$_3$)$_3$C), 1.41 (2H, m, CH$_3$CH$_2$), 1.34 (3H, d, J=6.5, PhCHCH$_3$), 0.85 (3H, t, J=7.3, CH$_3$CH$_2$); $\delta_C$ (50 MHz; CDCl$_3$) 172.19 (C=O), 146.44, (Ph:C$_{ipso}$), 128.53, 126.92 (Ph:C$_{ortho}$, C$_{meta}$), 126.84 (Ph:C$_{para}$), 80.23 (C(CH$_3$)$_3$), 55.01, 53.71 (CHN), 39.10 (CH$_2$CO), 28.04 (C(CH$_3$)$_3$), 27.78 (CH$_3$CH$_2$), 24.80 (NCHCH$_3$), 10.24 (CH$_3$CH$_2$); m/z (CI) 278 (MH$^+$, 100%), 248 (5), 222 (30), 192 (12), 162 (15), 105 (20); (Found: C, 73.84; H, 10.11; N, 4.93. C$_{17}$H$_{27}$NO$_2$ requires C, 73.61; H, 9.81; N, 5.05%).

EXAMPLE 17

(3R,αS)-t-Butyl 3-(α-methylbenzylamino)-4-hexenoate (32)

The title compound (32) was prepared from compound (12) of Example 4 using the above-described procedure. $[\alpha]_D^{21}$ −45.1 (c 1.69, CHCl$_3$); $\nu_{max}$(CHCl$_3$)/cm$^{-1}$ 1728 s (C=O); δH (300 MHz; CDCl$_3$) 7.32–7.18 (5H, m, Ph), 5.55 (1H, dq, J=15.2 and 6.4, CH$_3$CH=CH), 5.26 (ddq, J=15.2, 8.0 and 1.6, CH$_3$CH=CH), 3.84 (1H, q, J=6.5, PhCHCH$_3$), 3.45 (1H, m, NCHCH$_2$), 2.41, 2.35 (2H, ABX system, J$_{AB}$=14.5, J$_{AX}$=6.6, J$_{BX}$=6.5, CH$_2$CO), 1.65 (3H, dd, J=6.4 and 1.6, CH$_3$C=C), 1.45 (9H, s, (CH$_3$)$_3$C), 1.33 (3H, d, J=6.5, PhCHCH$_3$); $\delta_C$ (50 MHz; CDCl$_3$) 171.53 (C=O), 146.51 (Ph:C$_{ipso}$), 133.07 (CH$_3$C=C), 128.53, 126.82 (Ph:C$_{ortho}$, C$_{meta}$), 126.96 (Ph:C$_{para}$), 80.28 (C(CH$_3$)$_3$), 55.14, 54.57 (CHN), 41.78 (CH$_2$CO), 28.03 (C(CH$_3$)$_3$), 23.12 (NCHCH$_3$), 17.83 (CH$_3$C=C); m/z (CI) 290 (MH$^+$, 100%), 234 (30), 174 (45), 105 (35); (Found: C, 74.61; H, 9.63; N, 4.62. C$_{18}$H$_{27}$NO$_2$ requires C, 74.70; H, 9.40; N, 4.84%).

EXAMPLE 18

(3R,αS)-t-Butyl 3-(α-methylbenzylamino)-3-(fur-2-yl)propionate (33)

The title compound (33) was prepared from compound (14) of Example 5 using the above-described procedure. $[\alpha]_D^{21}$ −1.5 (c 1.74, CHCl$_3$); $\nu_{max}$(CHCl$_3$)/cm$^{-1}$ 1729 s (C=O); $\delta_H$ (300 MHz; CDCl$_3$) 7.32–7.20 (6H, m, Ph, OCH=CH), 6.28 (1H, dd, J=3.2 and 1.9, OCH=CH), 6.15 (1H, d, J=3.2, OCH=CH), 4.19 (1H, t, J=6.9, NCHCH$_2$), 3.76 (1H, q, J=6.5, PhCHCH$_3$); $\delta_C$ (50 MHz; CDCl$_3$) 170.93 (C=O), 156.00 (OC=CH), 146.15 (Ph:C$_{ipso}$), 141.78 (OCH=CH), 128.61, 126.81 (Ph:C$_{ortho}$, C$_{meta}$), 127.14 (Ph:C$_{para}$), 110.10 (OCH=CH), 106.40 (OC=CH), 80.55 (C(CH$_3$)$_3$), 54.97, 50.83 (CHN), 40.72 (CH$_2$CO), 27.96 (C(CH$_3$)$_3$), 23.04 (NCHCH$_3$); m/z (CI) 316 (MH$^+$, 100%), 260 (25), 200 (25), 154 (20), 120 (25), 105 (27); (Found: C, 72.37; H, 8.04; N, 4.31. C$_{19}$H$_{25}$NO$_3$ requires C, 72.35; H, 7.99; N, 4.44%).

EXAMPLE 19

(3R,αS)-t-Butyl 3-(α-methylbenzylamino)-4-methylpentanoate (34)

The title compound (34) was prepared from compound (16) of Example 6 using the above-described procedure. $[\alpha]_D^{21}$ −52.7 (c 1.57, CHCl$_3$); $\nu_{max}$(CHCl$_3$)/cm$^{-1}$ 1724 s (C=O); $\delta_H$ (300 Hz; CDCl$_3$) 7.38–7.21 (5H, m, Ph), 3.88 (1H, q, J=6.5, PhCHCH$_3$), 2.60 (1H, m, NCHCH$_2$), 2.38, 2.27 (2H, ABX system, $J_{AB}$=14.4, $J_{AX}$=5.4, $J_{BX}$=6.2, CH$_2$CO), 1.68 (1H, m, (CH$_3$)$_2$CH), 1.47 (9H, s, (CH$_3$)$_3$C), 1.33 (3H, d, J=6.5, PhCHCH$_3$), 0.89 (3H, d, J=6.8, (CH$_3$)$_2$CH), 0.81 (3H, d, J=6.8, (CH$_3$)$_2$CH); $\delta_C$ (50 MHz; CDCl$_3$) 172.67 (C=O), 146.58 (Ph:C$_{ipso}$), 128.42, 127.12 (Ph:C$_{ortho}$, C$_{meta}$), 126.95 (Ph:C$_{para}$), 80.19 (C(CH$_3$)$_3$), 57.82, 55.37 (CHN), 36.81 (CH$_2$CO), 31.14 ((CH$_3$)$_2$CH), 28.03 (C(CH$_3$)$_3$), 24.76 (NCHCH$_3$), 18.78, 18.32 ((CH$_3$)$_2$CH); m/z (CI) 292 (MH$^+$, 100%), 236 (20), 192 (20), 176 (17), 105 (20); (Found: C, 74.07; H, 10.31; N, 4.58. C$_{18}$H$_{29}$NO$_2$ requires C, 74.18; H, 10.03; N, 4.81%).

EXAMPLE 20

(3R,αS)-t-Butyl 3-(α-methylbenzylamino)-4-hexenoate (32)

To a solution of compound (12) from Example 4 (1.080 g, 3.28 mmol) in anhydrous dichloromethane (20 ml) was added tetrakis-(triphenylphosphine)-palladium (0) (0.040 g, 1 mol %) and N,N'-dimethylbarbituric acid (0.536, 9.85 mmol). This mixture was stirred at 40° C. for 2 hours, after which the dichloromethane was removed under reduced pressure. The residue was dissolved in diethyl ether (50 ml) and washed with saturated sodium bicarbonate solution (2×20 ml) and brine (20 ml) and dried (magnesium sulphate) and the solvent was removed under reduced pressure to yield a pale yellow oil. Purification by flash chromatography on silica gel [ethyl acetate/petroleum ether (4:9)] afforded the title compound (R$_f$ 0.30) as a colourless oil (0.950 g, 100%). $\delta_H$ (300 MHz; CDCl$_3$) 7.32–7.18 (5H, m, Ph), 5.55 (1H, dq, J=15.2 and 6.4, CH$_3$CH=CH), 5.26 (1H, ddq, J=15.2, 8.0 and 1.6, trans CH$_2$CH=CH), 3.84 (1H, q, J=6.5, PhCHCH$_3$), 3.45 (1H, m, NCHCH$_2$), 2.41 (1H, dd, J=14.5 and 6.6, CH$_2$CO$_2$), 2.35 (1H, dd, J=14.5 and 6.5, CH$_2$CO$_2$), 1.65 (3H, dd, J=6.4 and 1.6, CH$_3$C=C), 1.45 (9H, s, (CH$_3$)$_3$C), 1.33 (3H, d, J=6.5, PhCHCH$_3$).

Transesterification reactions

EXAMPLE 21

(3S,αS)-Methyl-3-(α-methylbenzylamino)butanoate (35)

A solution of compound (29) from Example 14 (1.00 mmol) was stirred in a saturated solution of gaseous hydrogen chloride in methanol for 30 minutes. The solvent was then removed under reduced pressure. This procedure was repeated until no starting material remained. The white solid residue was diluted with ethyl acetate (30 ml), washed with saturated aqueous sodium bicarbonate (2×30 ml), water (20 ml) and brine (20 ml), dried (magnesium sulphate) and filtered, and the solvent was evaporated under reduced pressure to give the title compound (35) as a clear oil. $[\alpha]_D^{21}$ −45.5 (c 1.95, CHCl$_3$); $\nu_{max}$(CHCl$_3$)/cm$^{-1}$ 1736 s (C=O); $\delta_H$ (300 MHz; CDCl$_3$) 7.34–7.20 (5H, m, Ph), 3.88 (1H, q, J=6.5, PhCHCH$_3$), 3.67 (3H, s, OCH$_3$), 2.99 (1H, m, CH$_3$CHCH$_2$), 2.47, 2.38 (2H, ABX system, $J_{AB}$=14.8, $J_{AX}$=5.4, $J_{BX}$=6.5, CH$_2$CO), 1.33 (3H, d, J=6.5 PhCHCH$_3$), 1.06 (3H, d, J=6.4, CH$_3$CHCH$_2$); $\delta_C$ (50 MHz; CDCl$_3$) 173.01 (C=O), 146.29 (Ph:C$_{ipso}$), 128.63, 126.70 (Ph:C$_{ortho}$, C$_{meta}$), 127.07 (Ph:C$_{para}$), 55.15, 47.69 (CHN), 51.30 (OCH$_3$), 40.52 (CH$_2$CO), 24.54, 21.34 (NCHCH$_3$); m/z (CI) 222 (MH$^+$, 100%), 206 (15), 148 (10), 118 (5), 105 (10); (Found: C, 70.48; H, 8.80. C$_{13}$H$_{19}$NO$_2$ requires C, 70.56; H, 8.65%).

EXAMPLE 22

(3R,αS)-Methyl 3-(α-methylbenzylamino)-3-phenylpropionate (36)

Following the procedure of Example 21 the title compound (36) was prepared from compound (30) of Example 15. $[\alpha]_D^{21}$ −14.9 (c 2.04, CHCl$_3$); $\nu_{max}$(CHCl$_3$)/cm$^{-1}$ 1738 s (C=O); $\delta_H$ (300 MHz; CDCl$_3$) 7.36–7.21 (10H, m, Ph), 4.23 (1H, dd, J=6.2 and 7.7, NCHCH$_2$), 3.69 (1H, q, J=6.5, PhCHCH$_3$), 3.64 (3H, s, OCH$_3$), 2.78, 2.68 (2H, ABX system, $J_{AB}$=15.2, $J_{AX}$=7.7, $J_{BX}$=6.2, CH$_2$CO), 1.37 (3H, d, J=6.5, PhCHCH$_3$); $\delta_C$ (50 MHz; CDCl$_3$) 172.51 (C=O), 146.25, 143.08 (Ph:C$_{ipso}$), 128.81, 128.64, 127.61, 127.17, 126.81 (Ph:C$_{ortho}$, C$_{meta}$, C$_{para}$), 56.82, 54.64 (CHN), 51.52 (OCH$_3$), 42.48 (CH$_2$CO), 22.26, (NCHCH$_3$); m/z (CI) 284 (MH$^+$, 100%), 268 (13), 236 (20), 210 (23), 106 (40); (Found: C, 76.06; H, 7.43; N, 4.84. C$_{18}$H$_{21}$NO$_2$ requires C, 76.30; H, 7.47; N, 4.94%).

EXAMPLE 23

(3S,αS)-Methyl 3-(α-methylbenzylamino)pentanoate (37)

Following the procedure of Example 21 the title compound (37) was prepared from compound (31) of Example 16. $[\alpha]_D^{21}$ −60.4 (c 1.77, CHCl$_3$); $\nu_{max}$(CHCl$_3$)/cm$^{-1}$ 1736 s (C=O); $\delta_H$ (300 MHz; CDCl$_3$) 7.36–7.18 (5H, m, Ph), 3.89 (1H, q, J=6.5, PhCHCH$_3$), 3.67 (3H, s, OCH$_3$), 2.73 (1H, m, NCHCH$_2$) 2.47, 2.39 (2H, ABX system, $J_{AB}$=14.7, $J_{AX}$=5.8, $J_{BX}$=5.6, CH$_2$CO), 1.41 (2H, m, CH$_3$CH$_2$), 1.33 (3H, d, J=6.6, PhCHCH$_3$), 0.86 (3H, t, J=7.4, CH$_3$CH$_2$); $\delta_C$ (50 MHz; CDCl$_3$) 173.22 (C=O), 146.29 (Ph:C$_{ipso}$), 128.55, 127.03, 126.86 (Ph:C$_{ortho}$, C$_{meta}$, C$_{para}$), 55.07, 53.44 (CHN), 51.29 (OCH$_3$), 37.99 (CH$_2$CO), 27.89 (CH$_3$CH$_2$), 24.80 (NCHCH$_3$), 10.20 (CH$_3$CH$_2$); m/z (CI) 236 (MH$^+$, 100%), 220 (10), 206 (15), 105 (20); Found: C, 71.08; H, 9.23; N, 5.81. C$_{14}$H$_{21}$NO$_2$ requires C, 71.46; H, 8.99; N, 5.95%).

EXAMPLE 24

(3R,αS)-Methyl 3-(α-methylbenzylamino)-4-hexenoate (38)

Following the procedure of Example 21 the title compound (38) was prepared from compound (32) of Example 17. $[\alpha]_D^{21}$ −48.5 (c 1.28, CHCl$_3$); $\nu_{max}$ (CHCl$_3$)/cm$^{-1}$ 1736 s (C=O), $\delta_H$ (300 MHz; CDCl$_3$) 7.32–7.20 (5H, m, Ph), 5.56 (1H, dq, J=15.2 and 6.4, CH$_3$CH=CH), 5.30 (1H, ddq, J=15.2, 8.0 and 1.6, CH$_3$CH=CH), 3.84 (1H, q, J=6.5, PhCHCH$_3$), 3.67 (3H, s, OCH$_3$), 3.49 (1H, m,NCHCH$_2$), 2.52, 2.46 (2H, ABX system, $J_{AB}$=18.9, $J_{AX}$=6.5, $J_{BX}$=6.5 CH$_2$CO), 1.65 (3H, dd, J=6.4 and 1.6, CH$_3$C=C), 1.32 (3H, d, J=6.5, PhCHCH$_3$); $\delta_C$ (50 MHz; CDCl$_3$) 172.67 (C=0), 146.36 (Ph:C$_{ipso}$), 132.82 (CH$_3$C=C), 128.57, 126.79 (Ph:C$_{ortho}$,C$_{meta}$), 127.14 (Ph:C$_{para}$), 54.76, 54.62 (CHN), 51.36 (OCH$_3$), 40.34 (CH$_2$CO), 23.12 (NCHCH$_3$), 17.59 (CH$_3$C=C); m/z (CI) 248 (MH$^+$, 100%), 232 (10), 174 (15), 105 (10) (Found: C, 72.89; H, 8.97. C$_{15}$H$_{21}$NO$_2$ requires C, 72.84; H,8.50%).

EXAMPLE 25

(3R,αS)-Methyl 3-(α-methylbenzylamino)-3-(fur-2-yl) propionate (39)

Following the procedure of Example 21 the title compound (39) was prepared from compound (33) of Example 18. $v_{max}$ (CHCl$_3$)/cm$^{-1}$ 1739 s (C=O), $\delta_H$ (300 MHz; CDCl$_3$) 7.32–7.18 (6H, m, Ph, OCH=CH), 6.29 (1H, dd, J=3.3 and 1.9, OCH=CH), 6.15 (1H, d, J=3.3, OCH=CH), 4.25 (1H, t, J=6.9, NCHCH$_2$), 3.76 (1H, q, J=6.5, PhCHCH$_3$), 3.67 (1H, s, OCH$_3$), 2.77 (2H, m, CH$_2$CO), 1.35 J=6.5, PhCHCH$_3$); $\delta_C$ (50 MHz; CDCl$_3$) 172.12 (C=O), 155.71 (OC=CH), 146.00 (Ph:C$_{ipso}$), 141.96 (OCH=CH), 128.64, 126.81 (Ph:C$_{ortho}$, C$_{meta}$), 127.21 (Ph:C$_{para}$), 110.18 (OCH=CH), 106.48 (OC=CH), 55.02, 51.58 (CHN), 50.53 (OCH$_3$), 39.28 (CH$_2$CO), 22.98 (NCHCH$_3$); m/z (CI) 274 (MH$^+$, 100%), 200 (20), 153 (20), 105 (25) (Found: C, 70.55; H, 7.03. C$_{16}$H$_{19}$NO$_3$ requires C, 70.31; H,7.01%).

EXAMPLE 26

(3R,αS)-Methyl 3-(α-methylbenzylamino)-4-methylpentanoate (40)

Following the procedure of Example 21 the title compound (40) was prepared from compound (34) of Example 19. [α]$_D^{21}$ −57.5 (c 1.87, CHCl$_3$); $v_{max}$ (CHCl$_3$)/cm$^{-1}$ 1736 s (C=O), $\delta_H$ (300 MHz; CDCl$_3$) 7.36–7.21 (5H, m, Ph), 3.85 (1H, q, J=6.5, PhCHCH$_3$), 3.68 (3H, s, OCH$_3$), 2.66 (1H, m, NCHCH$_2$), 2.47, 2.37 (2H, ABX system, J$_{AB}$=14.6, J$_{AX}$=5.4, J$_{BX}$=6.5, CH$_2$CO), 1.67 (1H, m, (CH$_3$)$_2$CH), 1.32 (3H, d, J=6.5, PhCHCH$_3$); 0.88 (3H, d, J=6.8, (CH$_3$)$_2$CH), 0.81 (3H, d, J=6.8, (CH$_3$)$_2$CH); $\delta_C$ (50 MHz; CDCl$_3$) 173.73 (C=O), 146.40 (Ph:C$_{ipso}$), 128.45, 127.06 (Ph:C$_{ortho}$, C$_{meta}$, C$_{para}$), 57.52, 55.44 (CHN), 51.36 (OCH$_3$), 35.75(CH$_2$CO), 31.31 [(CH$_3$)$_2$CH], 24.74 (NCHCH$_3$), 18.45, 18.36 [(CH$_3$)$_2$CH]; m/z (CI) 250 (MH$^+$, 100%), 236 (15), 206 (22), 105 (22); (Found: C, 71.91; H, 9.67. C$_{15}$H$_{23}$NO$_2$ requires C, 72.25; H,9.30%).

Cyclisation and other transformations

EXAMPLE 27

(4S,αS)-1-(α-Methylbenzyl)-4-methylazetidin-2-one (41)

To a solution compound (35) from Example 21 (1.00 mmol) in anhydrous diethyl ether (5 ml) at 0° C. was added slowly, dropwise, 3.0 M methylmagnesium bromide (1.10 mmol). The resulting solution was stirred for 10 minutes and the reaction was then quenched by addition of pH7 buffer. Diethyl ether (20 ml) was added, whereafter the solution was washed with water (20 ml) and brine (20 ml), dried (magnesium sulphate) and filtered. The solvent was removed under reduced pressure to afford the title compound (41) as a clear oil which was subjected to flash chromatography on silica gel. [α]$_D^{21}$ −68.9 (c 1.61, CHCl$_3$); $v_{max}$ (CHCl$_3$)/cm$^{-1}$ 1742 s (C=O), $\delta_H$ (300 MHz; CDCl$_3$) 7.34–7.23(5H, m, Ph), 4.92 (1H, q, J=7.2, PhCHCH$_3$), 3.51 (1H, m, CH$_3$CHCH$_2$); 2.97, 2.46 (2H, ABX system, J$_{AB}$=14.4, J$_{AX}$=5.1, J$_{BX}$=2.4, CH$_2$CO), 1.63 (3H, d, J=7.2, PhCHCH$_3$), 1.25 (3H, d, J=6.1, CH$_3$CHCH$_2$); $\delta_C$ (50 MHz; CDCl$_3$) 166.90 (C=O), 140.67 (Ph:C$_{ipso}$), 128.85, 127,18 (Ph:C$_{ortho}$, C$_{meta}$), 127.77 (Ph: C$_{para}$), 51.78, 47.18 (CHN), 43.45(CH$_2$CO), 20.65, 19.25 (NCHCH$_3$); m/z (CI) 190 (MH$^+$, 100%), 174(5), 132 (10), 105 (8); (Found: C, 76.02; H, 7.98; 7.07. C$_{12}$H$_{15}$NO requires C, 76.16; H, 7.99; N, 7.40%).

EXAMPLE 28

(4R,αS)-1-(α-Methylbenzyl)-4-phenylazetidin-2-one (42)

Following the procedure of Example 27 the title compound (42) was prepared from compound (36) of Example 22. [α]$_D^{21}$ +57.9 (c 1.06, CHCl$_3$); $v_{max}$ (CHCl$_3$)/cm$^{-1}$ 1747 s (C=O); $\delta_H$ (300 MHz; CDCl$_3$) 7.34–7.18 (10H, m, Ph), 5.05 (1H, q, J=7.2, PhCHCH$_3$), 4.30 (1H, dd, J=5.3 and 2.5, NCHCH$_2$), 3.25, 2.84 (2H, ABX system, J$_{AB}$=14.7, J$_{AX}$=5.3, J$_{BX}$=2.5, CH$_2$CO), 0.87 (3H, d, J=7.2, PhCHCH$_3$); $\delta_C$ (50 MHz; CDCl$_3$) 167.66 (C=O), 140.18, 139.99 (Ph:C$_{ipso}$), 128.93, 128.82, 127.48, 126.89 (Ph:C$_{ortho}$,C$_{meta}$), 128.63, 128.19 (Ph: C$_{para}$), 53.40 (CHN), 46.28(CH$_2$CO), 18.67 (NCHCH$_3$); m/z (CI) 252 (MH$^+$, 100%), 236 (4) 132 (10), 104 (60); (Found: C, 81.11 H, 6.96. C$_{11}$H$_{17}$NO requires C, 81.24; H, 6.82%).

EXAMPLE 29

(4S,αS)-1-(α-Methylbenzyl)-4-ethylazetidin-2-one (43)

Following the procedure of Example 27 the title compound (43) was prepared from compound (37) of Example 23. [α]$_D^{21}$ −8.9 (c 1.84, CHCl$_3$) $v_{max}$ (CHCl$_3$)cm$^{-1}$ 1742 s (C=O); $\delta_H$ (300 MHz; CDCl$_3$) 7.38–7.25 (5H, m, Ph), 4.88 (1H, q, J=7.2 PhCHCH$_3$), 3.34 (1H, m, NCHCH$_2$), 2.88 2.48 (2H, ABX system, J$_{AB}$=14.5, J$_{AX}$=5.1, J$_{BX}$=2.4, CH$_2$CO), 1.75 (1H, m, CH$_3$CH$_2$), 1.62 (3H, d, J=7.2, PhCHCH$_3$), 1.38 (1H, m, CH$_3$CH$_2$), 0.80 (3H, t, J=7.4, CH$_3$CH$_2$); $\delta_C$ (50 MHz; CDCl$_3$) 167.13(C=O), 140.85 (Ph:C$_{ipso}$), 128.81, 127.11 (Ph:C$_{ortho}$,C$_{meta}$), 127.69 (Ph: C$_{para}$), 52.72, 52.05 (CHN), 40.92 (CH$_2$CO), 27.07 CH$_3$CH$_2$), 19.48 (NCHCH$_3$), 9.11 (CH$_3$CH$_2$); m/z (CI) 204 (MH$^+$, 100%), 188 (5), 146 (6), 105 (10); (Found: C, 76.65; H, 8.67. C$_{13}$H$_{17}$NO requires C, 76.81; H, 8.43%).

EXAMPLE 30

(4R,αS)-1-(α-Methylbenzyl)-4-propenylazetidin-2-one (44)

Following the procedure of Example 27 the title compound (44) was prepared from compound (38) of Example 24. [α]$_D^{21}$ −39.4 (c 1.02, CHCl$_3$); $\delta_H$ (300 MHz; CDCl$_3$) 7.38–7.25(5H, m, Ph), 5.61 (1H, dq, J=15.2 and 6.4, CH$_3$CH=CH), 5.38 (1H, ddq, J=15.2, 8.0 and 1.6, CH$_3$CH=CH), 4.92 (1H, q, J=7.2, PhCHCH$_3$), 3.81 (1H, m, NCHCH$_2$), 2.99, 2.57 (2H, ABX system, J$_{AB}$=14.6, J$_{AX}$=5.2, J$_{BX}$=2.2, CH$_2$CO), 1.67 (3H, dd, J=6.4 and 1.6, CH$_3$C=C), 1.54 (3H, dd, J=7.2, PhCHCH$_3$).

EXAMPLE 31

(4R,αS)-1-(α-Methylbenzyl)-4-(fur-2-yl)-azetidin-2-one (45)

Following the procedure of Example 27 the title compound (45) was prepared from compound (39) of Example 25. [α]$_D^{21}$ +36.7 (c 1.96, CHCl$_3$); $v_{max}$(CHCl$_3$)/cm$^{-1}$ 1751 s (C=O); $\delta_H$ (300 MHz; CDCl$_3$) 7.39–7.23 (6H, m, Ph, OCH=CH), 6.33 (1H, dd, J=3.3 and 1.9, and OCH=CH), 6.21 (1H, d, J=3.3, OCH=CH), 5.00 (1H, q, J=7.2, PhCHCH$_3$), 4.38 (1H, m, NCHCH$_2$), 3.14 (2H, m, CH$_2$CO), 1.30 (3H, d, J=7.2, PhCHCH$_3$); $\delta_C$ (50 MHz; CDCl$_3$) 166.60 (C=O), 151.53 (OC=CH), 142.82 (Ph:C$_{ipso}$), 139.91 (OCH=CH), 128.72, 127.24 (Ph:C$_{ortho}$, C$_{meta}$), 121.74 (Ph:C$_{para}$), 110.69 (OCH=CH), 109.09 (OC=CH), 51.42, 45.97 (CHN), 42.44 (CH$_2$CO), 17.60 (NCHCH$_3$); m/z (CI) 242 (MH$^+$, 100%), 226 (4), 132 (8), 94 (40); Found: C, 74.45; H, 6.45. C$_{15}$H$_{15}$NO$_2$ requires C, 74.67; H, 6.27%).

EXAMPLE 32

(4R,αS)-1-(α-Methylbenzyl)-4-isopropylazetidin-2-one (46)

Following the procedure of Example 27 the title compound (46) was prepared from compound (40) of Example 26. $[\alpha]_D^{21}$ +26.1 (c 1.96, CHCl$_3$); $v_{max}$(CHCl$_3$)/cm$^{-1}$ 1741 s (C=O), $\delta_H$(300 MHz; CDCl$_3$) 7.38–7.25(5H, m, Ph), 4.83 (1H, q, J=7.2, PhCHCH$_3$), 3.36 (1H, m, NCHCH$_2$), 2.72, 2.57 (2H, ABX system, $J_{AB}$=14.7, $J_{AX}$=5.2, $J_{BX}$=2.7, CH$_2$CO), 1.88 (1H, m, (CH$_3$)$_2$CH), 1.65 (3H, d, J=7.2, PhCHCH$_3$), 0.83 (3H, d, J=6.8, (CH$_3$)$_2$CH), 0.79 (3H, d, J=6.8, (CH$_3$)CH); $\delta_C$ (50 MHz; CDCl$_3$) 167.73 (C=O), 141.09 (Ph:C$_{ipso}$), 128.78, 127.14 (Ph:C$_{ortho}$,C$_{meta}$), 127.62 (Ph: C$_{para}$), 56.72, 52.95 (CHN), 36.59 (CH$_2$CO), 29.16 ((CH$_3$)$_2$CH), 19.30, 18.83, 14.91 (NCHCH$_3$, (CH$_3$)$_2$CH); m/z (CI) 218 (MH$^+$1, 100%), 202 (10), 132 (10), 105 (15); (Found: C, 77.47; H, 8.96. C$_{14}$H$_{19}$NO requires C, 77.38; H, 8.81%).

EXAMPLE 33

(2S,4S,5S,αS)-2-Ethyl-3-(α-methylbenzyl)-4-phenyl-1,3-oxazolidine-5-carboxylic acid t-butyl ester (47)

To a solution of compound (27) from Example 12 (1.039 g, 2.73 mmol) in anhydrous toluene (25 ml) was added tris(triphenylphosphine) rhodium(I) chloride (126 mg, 5 mol %). This solution was refluxed for 4 hours whereafter the toluene was removed under reduced pressure. The residue was treated with diethyl ether, precipitating the catalyst, and the solution was passed through alumina grade 5. After removal of the solvent under reduced pressure, the resulting oil was purified by flash chromatography on silica gel [ethyl acetate/petroleum ether (1:19)] affording the title compound (R$_f$ 0.40) as a colourless oil (0.86 g, 83%). $\delta_H$ (300 MHz; CDCl$_3$) 7.33–7.18 (10H, m, Ph), 4.48 (1H, t, NCHO), 4.38 (1H, d, J=8.0, PhCHCH), 4.21 (1H, d, J=8.0, PhCHCH), 4.01 (1H, q, J=6.9, PhCHCH$_3$), 1.91 (2H, m, CHCH$_2$CH$_3$), 1.27 (3H, d, J=6.9, PhCHCH$_3$), 1.15 (3H, t, J=7.5, CHCH$_2$CH$_3$), 0.99 (9H, s, (CH$_3$)$_3$C).

EXAMPLE 34

(2S,3S,6R,αS)-3-Phenyl-4-(α-methylbenzyl)-6-iodomethyl-1,4-oxazine-2-carboxylic acid t-butyl ester (48)

To a solution of compound (27) from Example 12 (250 mg, 0.66 mmol) in tetrahydrofuran/water (9:1, 3 ml) at 0° C. was added N-iodosuccinimide (295 mg, 1.32 mmol). This solution was stirred at 0° C. for 2 hours. The resulting brown solution was poured into 1.0M aqueous sodium thiosulphate solution (20 ml) and this was washed with brine (20 ml), dried (magnesium sulphate) and filtered and the solvent was removed under reduced pressure to give a yellow oil. This was purified by flash chromatography on silica gel [ethyl acetate/petroleum ether (1:19)] to give the title compound (48) (R$_f$ 0.20) as a colourless oil (160 mg, 48%). $\delta_H$ (300 MHz; CDCl$_3$) 7.61–7.22 (10H, m, Ph), 4.65 (1H, d, J=3.7, CHCO$_2$), 4.36 (1H, d, J=3.7, NCHCH), 3.75–3.66 (1H, m, CHCH$_2$I), 3.33 (1H, q, J=6.4, PhCHCH$_3$), 3.31 (1H, dd, J=10.4 and 5.0, CH$_2$I), 3.24 (1H, dd, J=10.4 and 6.2, CH$_2$I), 2.58 (1H, dd, J=12.6 and 3.3, eq. NCH$_2$CH), 1.49 (3H, d, J=6.4, PhCHCH$_3$), 1.14 (9H, s, (CH$_3$)$_3$C).

Also recovered (R$_f$ 0.45) as a colourless oil was the corresponding (2S,3S,6S,αS) isomer (40 mg, 12%). $\delta_H$(300 MHz; CDCl$_3$) 7.56–7.21 (10H, m, Ph), 4.60 (1H, d, J=4.6, CHCO$_2$), 4.47–4.39 (1H, m, CHCH$_2$I), 4.29 (1H, d, J=4.6, PhCHCH), 3.65 (1H, q, J=6.5, PhCHCH$_3$), 3.50 (1H, dd, J=10.0 and 7.1, CH$_2$I), 3.37 (1H, dd, J=10.0 and 5.5, CH$_2$I), 2.45 (1H, dd, J=12.3 and 5.4, ax. NCH$_2$CH), 1.38 (3H, d, J=6.5, PhCHCH$_3$), 1.18 (9H, s, (CH$_3$)$_3$C).

EXAMPLE 35

(3R,2S,3'R,αR)-t-Butyl-2-hydroxyethyl-3-(N-allyl-α-methylbenzylamino)-4-pentenoate (49)

A solution of diisopropylamine (0.930 ml, 6.6 mmol) in anhydrous tetrahydrofuran (10 ml) was cooled to -78° C. prior to the dropwise addition of 1.6M butyllithium (3.54 ml, 5.7 mmol) via a syringe. The solution was warmed to 0° C. and stirred for 15 minutes. A solution of compound (26) from Example 11 (0.595 g, 1.9 mmol) in tetrahydrofuran (20 ml) was then added dropwise via a cannula and the solution was stirred at 0° C. for a further 2 hours. The reaction mixture was then cooled to -78° C. and trimethyl borate (0.539 ml, 5.7 mmol) was added dropwise via a syringe and the solution was stirred for 15 minutes. Acetaldehyde (1.10 ml, 19.9 mmol) was then added and the solution was stirred for 30 minutes before quenching the reaction with saturated aqueous ammonium chloride solution. Ethyl acetate (50 ml) was added, followed by brine (10 ml). The organic layer was separated, dried (magnesium sulphate) and filtered and the solvent was evaporated under reduced pressure to afford a yellow oil. This was purified by flash chromatography on silica gel [ethyl acetate/petroleum ether (1:9)] affording the title compound (49) (R$_f$ 0.25) as a colourless oil (0.332 g, 49%) and a mixture of the title compound and the second major diastereoisomer as a colourless oil (0.20 g, 30%). $\delta_H$ (300 MHz; CDCl$_3$) 7.37–7.20 (5H, m, Ph), 6.10 (1H, dt, J=17.1 and 10.1, CH$_2$=CHCH), 5.76 (1H, m, CH$_2$CH=CH$_2$), 5.30 (1H, dd, J=10.2 and 1.7, cis CH$_2$CH=CH$_2$), 5.20 (1H, dd, J=17.1 and 1.7, trans CH$_2$CH=CH$_2$), 5.00 (2H, m, CH$_2$=CHCH), 4.78 (1H, br s, OH), 4.21 (1H, q, J=6.8, PhCHCH$_3$), 4.10 (1H, dq, J=8.5 and 6.1, CH$_3$CHOH), 3.78 (1H, dd, J=10.1 and 6.8, NCHCH), 3.27 (1H, dd, J=15.4 and 5.9, NCH$_2$), 3.13 (1H, dd, J=15.4 and 7.3, NCH$_2$), 2.86 (1H, dd, J=8.5 and 6.8, CHCO$_2$), 1.45 (9H, s, (CH$_3$)$_3$C), 1.36 (3H, d, J=6.8, PhCHCH$_3$), 1.19 (3H, d, J=6.1, CH$_3$CHOH).

EXAMPLE 36

(2S,4R,5S,6R,αR)-2-Ethyl-3-(α-methylbenzyl)-4-vinyl-6-methyl-1,3-oxazine-5-carboxylic acid t-butyl ester (50)

Compound (49) from Example 35 (0.246 g, 0.69 mmol) was treated with tri(triphenylphosphine)rhodium(I) chloride (0.032 g, 0.034 mmol) in accordance with the procedure of Example 33. Flash chromatography of the product on silica gel [ethyl acetate/petroleum ether (1:19)] afforded the title compound (R$_f$ 0.40) as a colourless oil (0.182 g, 74%). $\delta_H$ (300 MHz, CDCl$_3$) 7.51–7.23 (5H, m, Ph), 5.94 (1H, ddd, J=16.9, 10.3 and 5.4, CH$_2$=CHCH), 5.36 (1H, app. dt. J=16.9 and 2.1, trans CH$_2$CH), 5.20 (1H, app. dt, J=10.3 and 2.1, cis CH$_2$=CH), 4.55 (1H, q, PhCHCH$_3$), 4.39 (1H, app. t, J=6.5, NCHO), 3.87 (1H, app. tt, J=5.8 and 1.9, CH$_2$=CHCH), 3.68 (1H, dq, J=10.9 and 5.9, CHCH$_3$O), 2.00–1.89 (1H, m, CH$_2$CH$_3$), 1.34 (9H, s, (CH$_3$)$_3$C), 1.30 (1H, m, J=6.8, CH$_2$CH$_3$), 1.13 (1H, dd, J=10.9 and 6.1, CHCO$_2$), 1.03 (3H, t, J=7.4, CHCH$_2$CH$_3$), 0.89 (3H, d, J=5.9, CHCH$_3$O).

EXAMPLE 37

(2S,3R,αS)-t-Butyl 2-methyl-3-(N-allyl-α-methylbenzylamino)-3-phenylpropanoate (51)

A solution of diisopropylamine (0.691 ml, 4.93 mmol) in anhydrous tetrahydrofuran (10 ml) was cooled to -78° C.

prior to the dropwise addition of 1.6M butyllithium (2.57 ml, 4.11 mmol) via a syringe. The solution was warmed to 0° C. and then immediately recooled to −78° C., whereupon a solution of compound (8) from Example 2 (600 mg, 1.64 mmol) in tetrahydrofuran (10 ml) was added dropwise via a cannula. Stirring was continued for 1 hour at −78° C. followed by the rapid injection of methyl iodide (0.512 ml, 8.22 mmol). The reaction mixture was allowed to warm slowly to room temperature overnight (16 hours) after which the solvent was evaporated. The residue was partitioned between ethyl acetate (50 ml) and brine (25 ml) and the organic layer was dried (magnesium sulphate), filtered and evaporated to yield a yellow oil. This was purified by flash chromatography on silica gel [ethyl acetate/petroleum ether (1:49)] affording the title compound (51) in 94% diastereoisomeric excess ($R_f$ 0.25) as a colourless oil (406 mg, 65%). $\delta_H$ (300 MHz, CDCl$_3$) 7.41–7.17 (10H, m, Ph), 5.93–5.79 (1H, m, NCH$_2$CH=CH$_2$), 5.11 (1H, app. dd, J=17.3 and 1.3, trans CH=CH$_2$), 5.08 (1H, app. dd, J=10.1 and 1.1, cis CH=CH$_2$), 4.18 (1H, d, J=11.4, PhCHCH$_3$), 3.29 (1H, app. ddt, J=14.7, 5.0 and 1.9, NCH$_2$), 3.19 (1H, dq, J=11.4 and 6.9, CHCHCH$_3$), 3.10 (1H, dd, J=14.7 and 8.0, NCH$_2$), 1.50 (9H, s, (CH$_3$)$_3$C), 0.94 (3H, d, J=6.7, PhCHCH$_3$), 0.90 (3H, d, J=6.9, CHCHCH$_3$).

EXAMPLE 38

(2S,2R,3'S,αS)-t-Butyl 2-hydroxyethyl-3-(N-allyl-α-methylbenzylamino)-4-hexenoate (52)

Compound (12) from Example 4 (0.2 g, 0.61 mmole) was treated in accordance with the procedure of Example 35, using diisopropylamine (0.298 ml, 2.13 mmol), 1.6M butyllithium (1.140 ml, 1.82 mmol), trimethyl borate (0.207 ml, 1.82 mmol) and acetaldehyde (0.340 ml, 6.08 mmol). Flash chromatography on silica gel [ethyl acetate/petroleum ether (1:9)] afforded the title compound (52) and the second major diastereoisomer ($R_f$ 0.30) as a colourless oil (0.173 g, 76%). $\delta_H$ (500 MHz; CDCl$_3$) 7.38–7.20 (5H, m, Ph), 5.80–5.70 (2H, m, NCH$_2$CH=CH$_2$ and CH$_3$CH=CH), 5.60 (1H, dq, J=15.3 and 6.3, CH$_3$CH=CH), 5.00 (2H, m, NCH$_2$CH=CH$_2$), 4.22 (1H, q, J=6.8, PhCHCH$_3$), 4.12 (1H, dq, J=6.1 and 8.8, CH$_3$CHOH), 3.75 (1H, dd, J=10.0 and 6.3, NCHCH), 3.25 (1H, dd, J=15.4 and 6.0, NCH$_2$), 2.81 (1H, dd, J=8.8 and 6.3, CH$_2$CO$_2$), 1.74 (3H, dd, J=6.3 and 1.4, CH$_3$CH=CH), 1.44 (9H, s, (CH$_3$)$_3$C), 1.35 (3H, d, J=6.7, PhCHCH$_3$), 1.18 (3H, d, J=6.1, CH$_3$CHOH).

EXAMPLE 39

(3S,2R,3'S,αS)-t-Butyl 2-hydroxyethyl-3-(N-allyl-α-methylbenzylamino)-5-phenyl-4-pentenoate (53)

Compound (20) from Example 8 (0.250 g, 0.64 mmol) was treated in accordance with the procedure of Example 35, using diisopropylamine (0.314 ml, 2.24 mmol), 1.6M butyllithium (1.20 ml, 1.92 mmol) and acetaldehyde (0.36 ml, 6.40 mmol). Flash chromatography on silica gel [ethyl acetate/petroleum ether (1:9)] afforded the title compound (53) and the second major diastereoisomer ($R_f$ 0.30) as a colourless oil (0.206 g, 74%). $\delta_H$ (300 MHz; CDCl$_3$) 7.41–7.22 (10H, m, Ph), 6.49 (1H, d, J=16.0, PhCH=CH), 6.24 (1H, dd, J=16.0 and 9.4, PhCH=CHCH), 5.91–5.76 (1H, m, NCH$_2$CH=CH$_2$), 5.18–5.02 (2H, m, NCH$_2$CH=CH$_2$), 4.31 (1H, q, J=6.8 and 1.5, PhCHCH$_3$), 4.19 (1H, dq, J=8.3 and 6.2, CH$_3$CHOH), 3.98 (1H, app. dt, J=7.2 and 1.9, NCHCH), 3.34–319 (2H, m, NCH$_2$CH=CH$_2$), 2.98 (1H, dd, J=8.3 and 6.9, CH$_2$CO$_2$), 1.44 (9H, s, (CH$_3$)$_3$C), 1.42 (3H, d, J=6.8, PhCHCH$_3$), 1.24 (3H, d, J=6.2, CH$_3$CHOH).

EXAMPLE 40

(2S,3S,αS)-t-Butyl 3-(N-cinnamoyl-α-methylbenzylamino)-2-hydroxy-3-phenylpropionate (54)

Compound (28) from Example 13 (0.200 g, 0.44 mmol) was treated with N-iodosuccinimide (0.197 g, 0.88 mmol) using standard iodoetherification conditions. Flash chromatography of the product on silica gel [ethyl acetate/petroleum (1:9)] afforded the title compound (54) ($R_f$ 0.50) as a yellow oil (0.093 g, 45%). $\delta_H$ (200 MHz; CDCl$_3$) 7.72 (1H, d, J=16.0, CH=CHPh), 7.57–7.22 (15H, m, Ph), 6.51 (1H, d, J=16.0, PhCH=CH), 5.45 (1H, d, J=4.9, CHCHOH), 4.25 (1H, d, J=4.9, PhCHCH), 3.81 (1H, d, J=6.5, PhCHCH$_3$), 1.92 (1H, br s, OH), 1.34 (3H, d, J=6.5, PhCHCH$_3$), 1.32 (9H, s, (CH$_3$)$_3$C). The corresponding 3-(α-methylbenzylamino) derivative ($R_f$ 0.25) was also recovered as a colourless oil (0.045 g, 30%). δH (200 MHz; CDCl$_3$) 7.48–7.14 (10H, m, Ph), 4.50 (1H, d, J=3.8, CHCHOH), 4.09 (1H, d, J=3.8, PhCHCH), 3.76 (1H, q, J=6.6, PhCHCH$_3$), 1.38 (3H, d, J=6.6, PhCHCH$_3$), 1.31 (9H, s, (CH$_3$)$_3$C).

We claim:

1. A compound of formula (I)

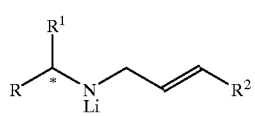

(I)

wherein R is a carbocyclic aryl group; $R^1$ is a $C_{1-10}$ alkyl, $C_{2-10}$ alkenyl, $C_{3-10}$ cycloalkyl, $C_{3-10}$ cycloalkyl-$C_{1-4}$ alkyl or $C_{6-12}$ aryl-$C_{1-4}$ alkyl group; $R^2$ is a hydrogen atom, a $C_{1-10}$ alkyl, $C_{2-10}$ alkenyl or $C_{6-20}$ carbocyclic aryl group or a heterocyclic group containing one or more 5- and/or 6-membered rings and at least one heteroatom selected from the group consisting of O, N and S; and the asterisk denotes that the group $R^1$ is predominantly in the R- or S-configuration such that the compound is in substantially enantiomerically pure form.

2. A compound as claimed in claim 1 comprising at least 95% of a single enantiomer.

3. A compound as claimed in claim 1 wherein R is phenyl or naphthyl optionally substituted by one or more substituents selected from the group consisting of halo, hydroxy, $C_{1-4}$ alkoxy, $C_{1-4}$ alkylthio, $C_{1-4}$ alkylsulphonyl, amino, substituted amino, carboxy, cyano, $C_{1-4}$ alkoxycarbonyl, carbamoyloxy, sulphamoyl and sulphoxy.

4. A compound as claimed in claim 3 wherein R is phenyl or 3,4-dimethoxyphenyl.

5. A compound as claimed in claim 1 wherein $R^1$ is methyl.

6. A compound as claimed in claim 1 wherein $R^2$ is selected from the group consisting of methyl, ethyl, propyl, butyl, vinyl, phenyl, naphthyl, furyl, thienyl, pyrrolyl, pyridyl, benzothienyl, indolyl, imidazolidinyl and piperidinyl groups.

7. A compound as claimed in claim 1 wherein $R^2$ is a hydrogen atom or a phenyl group.

8. The lithium amides of (S)-N-allyl-α-methylbenzylamine; (S)-(E,E)-N-hexa-2,4-dienyl-α-methylbenzylamine, and (S0-N-cinnamyl-α-methylbenzylamine.

9. A solution of a compound as claimed in claim 1.

10. A process for the preparation of a compound of formula (I)

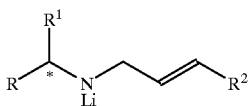

(I)

wherein R is carbocyclic aryl group; $R^1$ is a $C_{1-10}$ alkyl, $C_{2-10}$ alkenyl, $C_{3-10}$ cycloalkyl, $C_{3-10}$ cycloalkyl-$C_{1-4}$ alkyl or $C_{6-12}$ aryl-$C_{1-4}$ alkyl group; $R^2$ is a hydrogen atom, a $C_{1-10}$ alkyl, $C_{2-10}$ alkenyl or $C_{6-20}$ carbocyclic aryl group or a heterocyclic group containing one or more 5- and/or 6-membered rings and at least one heteroatom selected from the group consisting of O, N and S; and the asterisk denotes that the group $R^1$ is predominantly in the R- or S-configuration such that the compound is in substantially enantiomerically pure form, which process comprises reacting a compound of formula (V)

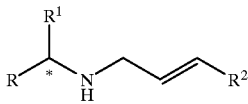

(V)

with a lithium alkyl.

11. In a method which comprises reacting a compound with an α,β-unsaturated carboxylic acid derivative so as to achieve a stereoselective Michael addition thereto wherein the improvement comprises using a compound of formula (I)

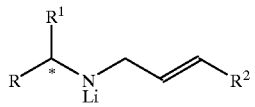

(I)

wherein R is a carbocyclic aryl group; $R^1$ is a $C_{1-10}$ alkyl, $C_{2-10}$ alkenyl, $C_{3-10}$ cycloalkyl, $C_{3-10}$ cycloalkyl-$C_{1-4}$ alkyl or $C_{6-12}$ aryl-$C_{1-4}$ alkyl group; $R^2$ is a hydrogen atom, a $C_{1-10}$ alkyl, $C_{2-10}$ alkenyl or $C_{6-20}$ carbocyclic aryl group or a heterocyclic group containing one or more 5- and/or 6-membered rings and at least one heteroatom selected from the group consisting of O, N and S; and the asterisk denotes that the group $R^1$ is predominantly in the R- or S-configuration such that the compound is in substantially enantiomerically pure form in said reaction.

12. A method as claimed in claim 11 wherein the product of the Michael addition is subjected to cleavage of the allylic N-substituent $R^2$.CH:CH.$CH_2$— and cyclisation to form a β-lactam.

* * * * *